(12) United States Patent
Hosogoe

(10) Patent No.: US 11,638,515 B2
(45) Date of Patent: May 2, 2023

(54) ENDOSCOPE, RISING BASE, CAP FOR ENDOSCOPE, METHOD FOR ATTACHING CAP FOR ENDOSCOPE, AND METHOD FOR DETACHING CAP FOR ENDOSCOPE

(71) Applicant: HOYA CORPORATION, Tokyo (JP)

(72) Inventor: Yoshitsugu Hosogoe, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 305 days.

(21) Appl. No.: 16/957,251

(22) PCT Filed: Dec. 27, 2018

(86) PCT No.: PCT/JP2018/048053
§ 371 (c)(1),
(2) Date: Jun. 23, 2020

(87) PCT Pub. No.: WO2019/131838
PCT Pub. Date: Jul. 4, 2019

(65) Prior Publication Data
US 2020/0390316 A1 Dec. 17, 2020

(30) Foreign Application Priority Data
Dec. 27, 2017 (JP) .............................. JP2017-252160

(51) Int. Cl.
*A61B 1/00* (2006.01)
*A61B 1/12* (2006.01)
*A61B 1/273* (2006.01)

(52) U.S. Cl.
CPC ...... *A61B 1/00098* (2013.01); *A61B 1/00101* (2013.01); *A61B 1/00137* (2013.01); *A61B 1/121* (2013.01); *A61B 1/2736* (2013.01)

(58) Field of Classification Search
CPC ............ A61B 1/00089; A61B 1/00098; A61B 1/00101; A61B 1/00137
See application file for complete search history.

(56) References Cited

U.S. PATENT DOCUMENTS

| | | | |
|---|---|---|---|
| 5,562,600 A | 10/1996 | Matsuno | |
| 5,569,157 A | 10/1996 | Nakazawa et al. | |

(Continued)

FOREIGN PATENT DOCUMENTS

| | | | |
|---|---|---|---|
| JP | 7-194516 A | 8/1995 | |
| JP | 8-56900 A | 3/1996 | |

(Continued)

OTHER PUBLICATIONS

International Search Report (ISR) dated Mar. 26, 2019 filed in PCT/JP2018/048053.

*Primary Examiner* — Matthew J Kasztejna
(74) *Attorney, Agent, or Firm* — Greenblum & Bernstein, P.L.C.

(57) ABSTRACT

To provide an endoscope that can be easily cleaned by dismounting an elevator after endoscopic examination. The endoscope includes a lever that is rotatably provided at a distal tip of an insertion portion (30), an elevator (80) that can be attached to and detached from the distal tip of the insertion portion (30), and includes a lever connection portion connected to the lever, and an elevator shaft (82) arranged to rotate coaxially with the lever when the lever connection portion and the lever are connected, and an endoscope cap (50) that can be attached to and detached from the distal tip of the insertion portion (30), and includes a bottomed cylindrical cover (52), an elevator support portion (761) that is provided inside the cover (52) and has an inlet through which the elevator shaft (82) enters when mounted to the distal tip of the insertion portion (30), and an elevator pivot portion (764) provided at the inlet.

6 Claims, 22 Drawing Sheets

(56) References Cited

U.S. PATENT DOCUMENTS

| | | | | |
|---|---|---|---|---|
| 5,674,181 | A | * | 10/1997 | Iida ........................ A61B 1/018 |
| | | | | 600/125 |
| 8,465,416 | B2 | * | 6/2013 | Kitano ................... A61B 1/018 |
| | | | | 600/106 |
| 10,149,604 | B2 | * | 12/2018 | Hiraoka .................... A61B 1/00 |
| 2002/0091303 | A1 | * | 7/2002 | Ootawara ................ A61B 1/01 |
| | | | | 600/106 |
| 2016/0270636 | A1 | | 9/2016 | Iwasaka et al. |
| 2018/0249894 | A1 | * | 9/2018 | Kolberg ............. A61B 1/00137 |
| 2019/0117045 | A1 | | 4/2019 | Hosogoe ............ A61B 1/00137 |
| 2019/0223697 | A1 | * | 7/2019 | Hosogoe ............ A61B 1/00101 |
| 2019/0223698 | A1 | | 7/2019 | Hosogoe et al. |
| 2019/0246886 | A1 | * | 8/2019 | Harada .................. A61B 1/018 |

FOREIGN PATENT DOCUMENTS

| | | |
|---|---|---|
| JP | 2002-17655 A | 1/2002 |
| JP | 2016-174822 A | 10/2016 |
| WO | 2018/070508 A1 | 4/2018 |

* cited by examiner

ENDOSCOPE, RISING BASE, CAP FOR ENDOSCOPE, METHOD FOR ATTACHING CAP FOR ENDOSCOPE, AND METHOD FOR DETACHING CAP FOR ENDOSCOPE

TECHNICAL FIELD

The present invention relates to an endoscope, an elevator, an endoscope cap, a mounting method of the endoscope cap, and a dismounting method of the endoscope cap.

BACKGROUND ART

An endoscope including an elevator at a distal tip of a channel passing through the inside of an insertion portion has been used. The elevator is used at the time of bending a treatment tool or the like that has passed through the channel and guiding the treatment tool in a desired direction.

An endoscope provided with a wall between an elevation wire that moves an elevator and the elevator is disclosed (Patent Literature 1).

CITATION LIST

Patent Literature

Patent Literature 1: JP 8-56900 A

SUMMARY OF INVENTION

Technical Problem

In the endoscope disclosed in Patent Literature 1, it takes time and effort for cleaning since a structure around the elevator is complicated.

In one aspect, an object of the invention is to provide an endoscope or the like that can be easily cleaned by dismounting an elevator after endoscopic examination.

Solution to Problem

An endoscope includes a lever that is rotatably provided at a distal tip of an insertion portion, an elevator that can be attached to and detached from the distal tip of the insertion portion, and includes a lever connection portion connected to the lever, and an elevator shaft arranged to rotate coaxially with the lever when the lever connection portion and the lever are connected, and an endoscope cap that can be attached to and detached from the distal tip of the insertion portion, and includes a bottomed cylindrical cover, an elevator support portion that is provided inside the cover and has an inlet through which the elevator shaft enters when mounted to the distal tip of the insertion portion, and an elevator pivot portion provided at the inlet.

Advantageous Effects of Invention

In one aspect, it is possible to provide an endoscope or the like that is easy to clean by dismounting an elevator after endoscopic examination.

DESCRIPTION OF EMBODIMENTS

First Embodiment

Figure 1:
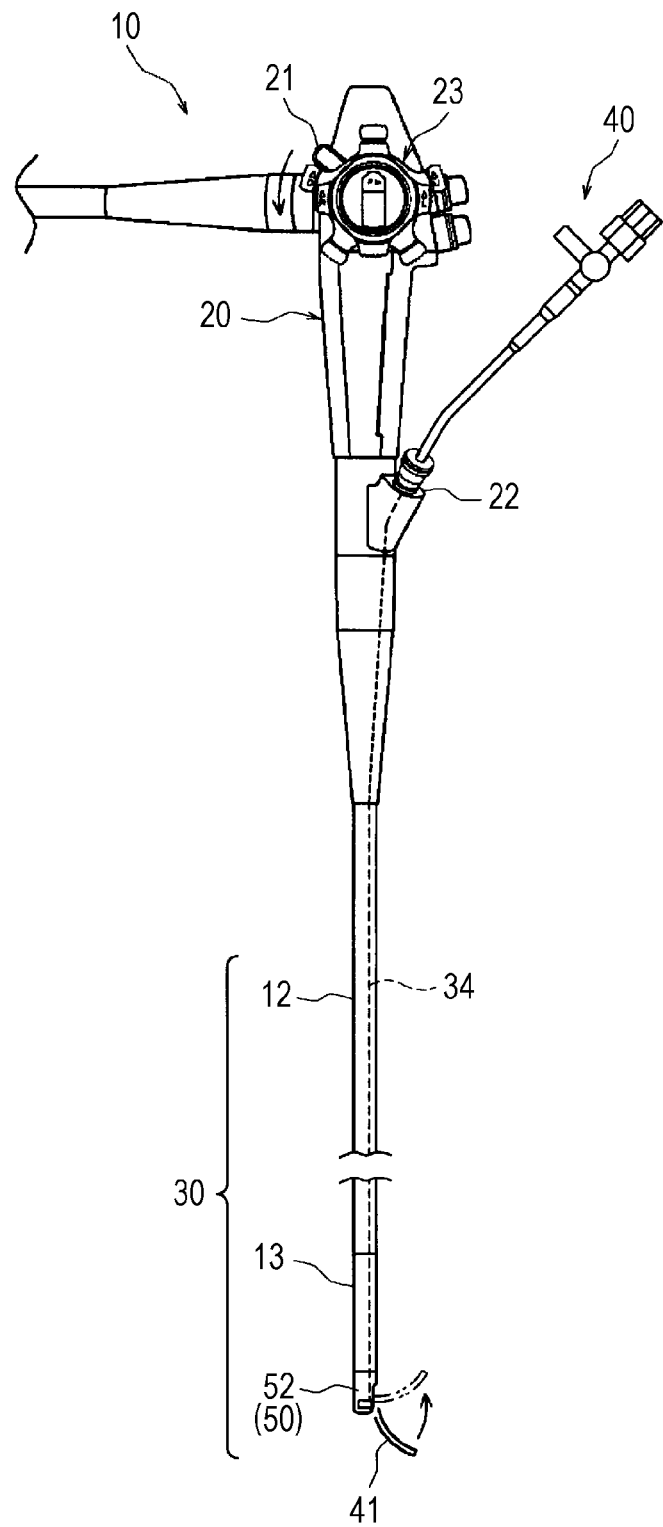
FIG. 1 is an exterior view of an endoscope.

FIG. 1 is an exterior view of an endoscope. An endoscope 10 of this embodiment is a flexible scope for an upper gastrointestinal tract. The endoscope 10 includes an operation unit 20 and an insertion portion 30. The operation unit 20 includes an elevation operation lever 21, a channel inlet 22, and a bending knob 23. The operation unit 20 is connected to a video processor (not illustrated), a light source device, a display device, and the like.

The insertion portion 30 is long and has one end connected to the operation unit 20. The insertion portion 30 includes a soft portion 12, a bending section 13, and an endoscope cap 50 in this order from the operation unit 20 side. The soft portion 12 is soft. The bending section 13 is bent according to an operation of the bending knob 23. The endoscope cap 50 covers a hard distal tip 31 (see FIG. 2) continuous with the bending section 13.

In the following description, a longitudinal direction of the insertion portion 30 is referred to as an insertion direction. Similarly, a side close to the operation unit 20 along the insertion direction is referred to as an operation unit side, and a side far from the operation unit 20 is referred to as a distal tip side.

Figure 2:
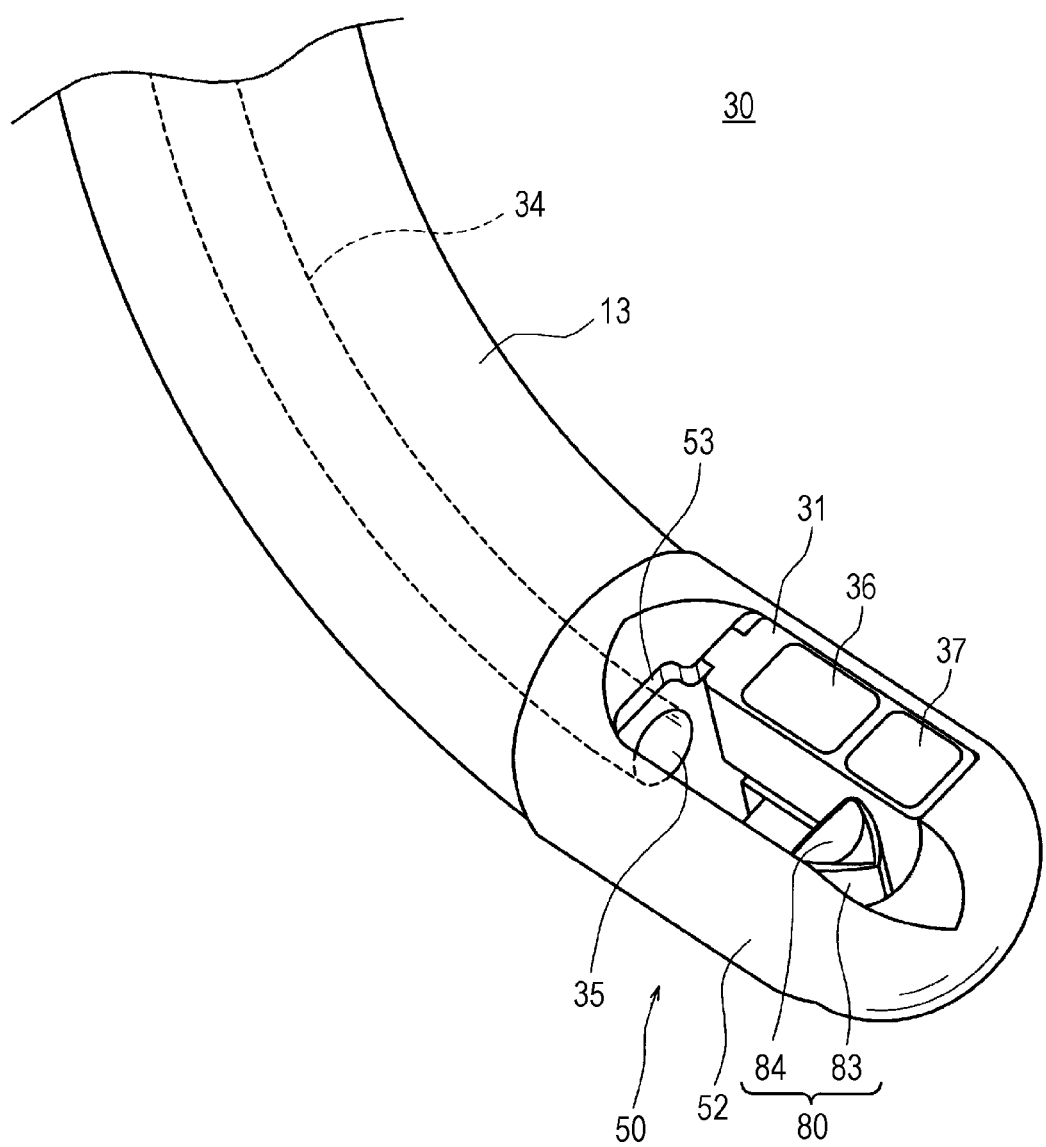
FIG. 2 is a perspective view of a distal tip of an insertion portion.
Figure 3:
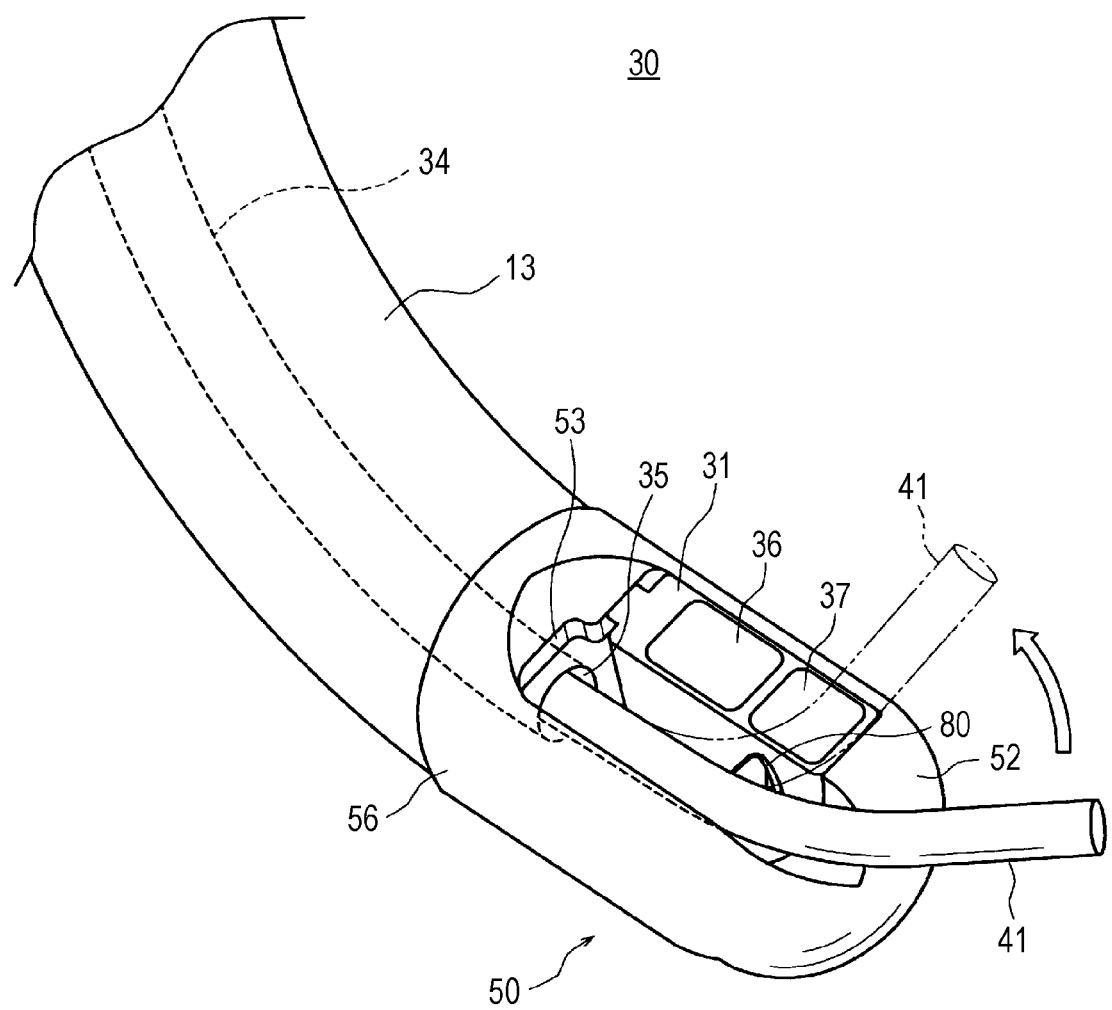
FIG. 3 is an explanatory view illustrating a state where a treatment tool distal tip protrudes from the distal tip of the insertion portion.

FIG. 2 is a perspective view of a distal tip of the insertion portion 30. FIG. 3 is an explanatory view illustrating a state where a treatment tool distal tip 41 protrudes from the distal tip of the insertion portion 30. The configuration of the endoscope 10 according to this embodiment will be described with reference to FIGS. 1 to 3.

The distal tip 31 arranged at a distal tip of the bending section 13 has an observation window 36 and an illumination window 37 arrayed side by side on one side along the insertion direction. The illumination window 37 is arranged closer to the distal tip side than the observation window 36. The distal tip 31 has a channel outlet 35 on the operation unit side on the other side. An elevation portion 83 is arranged on the distal tip side of the channel outlet 35. The cover 52 covering the distal tip 31 has a substantially rectangular window portion 53 in a portion corresponding to the observation window 36, the illumination window 37, and the elevation portion 83. The side of the window portion 53 on the operation unit side has a stepped shape in which the elevation portion 83 is located on the operation unit side and the observation window 36 is located on the distal tip side.

The illumination window 37 performs irradiation with illumination light emitted from a light source device (not illustrated). It is possible to optically observe a range illuminated by the illumination light through the observation window 36. The endoscope 10 of this embodiment is of a so-called side-view type in which a viewing direction in which optical observation is possible intersects the insertion direction. The endoscope 10 may be of a front oblique-view type in which the viewing direction is slightly inclined toward the distal tip side or a rear oblique-view type in which the viewing direction is slightly inclined toward the operation unit side.

The channel inlet 22 and the channel outlet 35 are connected by a channel 34 passing through the inside of the soft portion 12 and the bending section 13. As a treatment tool 40 is inserted from the channel inlet 22 from a side of the treatment tool distal tip 41, the treatment tool distal tip 41 can protrude from the channel outlet 35.

The treatment tool distal tip 41 protrudes while loosely curving on the elevation portion 83 as indicated by the solid line in FIG. 3. When the elevation operation lever 21 is operated as indicated by the arrow in FIG. 1, a lever 60 (see FIG. 8) moves as will be described later, and an elevator 80 moves in conjunction with the lever 60. As the elevator 80 moves, the treatment tool distal tip 41 on the elevator 80 is bent toward the operation unit 20 as indicated by the arrows and two-dot chain lines in FIGS. 1 and 3. The movement of the treatment tool distal tip 41 is captured by an image sensor or the like (not illustrated) through the observation window 36, and is displayed on the display device (not illustrated).

The treatment tool 40 is a treatment tool such as a high-frequency knife, a forceps, and a contrast tube. Incidentally, the instrument to be inserted into the channel 34 is not limited to the instrument for treatment. For example, an instrument for observation such as an ultrasonic probe and a microscopic endoscope may be inserted into the channel 34 for use. In the following description, the instrument for observation is also referred to as the treatment tool 40.

In the following description, the movement of the elevator 80 as described above may be expressed as "the elevator 80 rises". In the following description, an operation in which the treatment tool distal tip 41 is pushed by the raised elevator 80 and is bent may be referred to as "the treatment tool 40 rises". It is possible to adjust the degree of the rise of the treatment tool 40 by the operation of the elevation operation lever 21.

Figure 4:
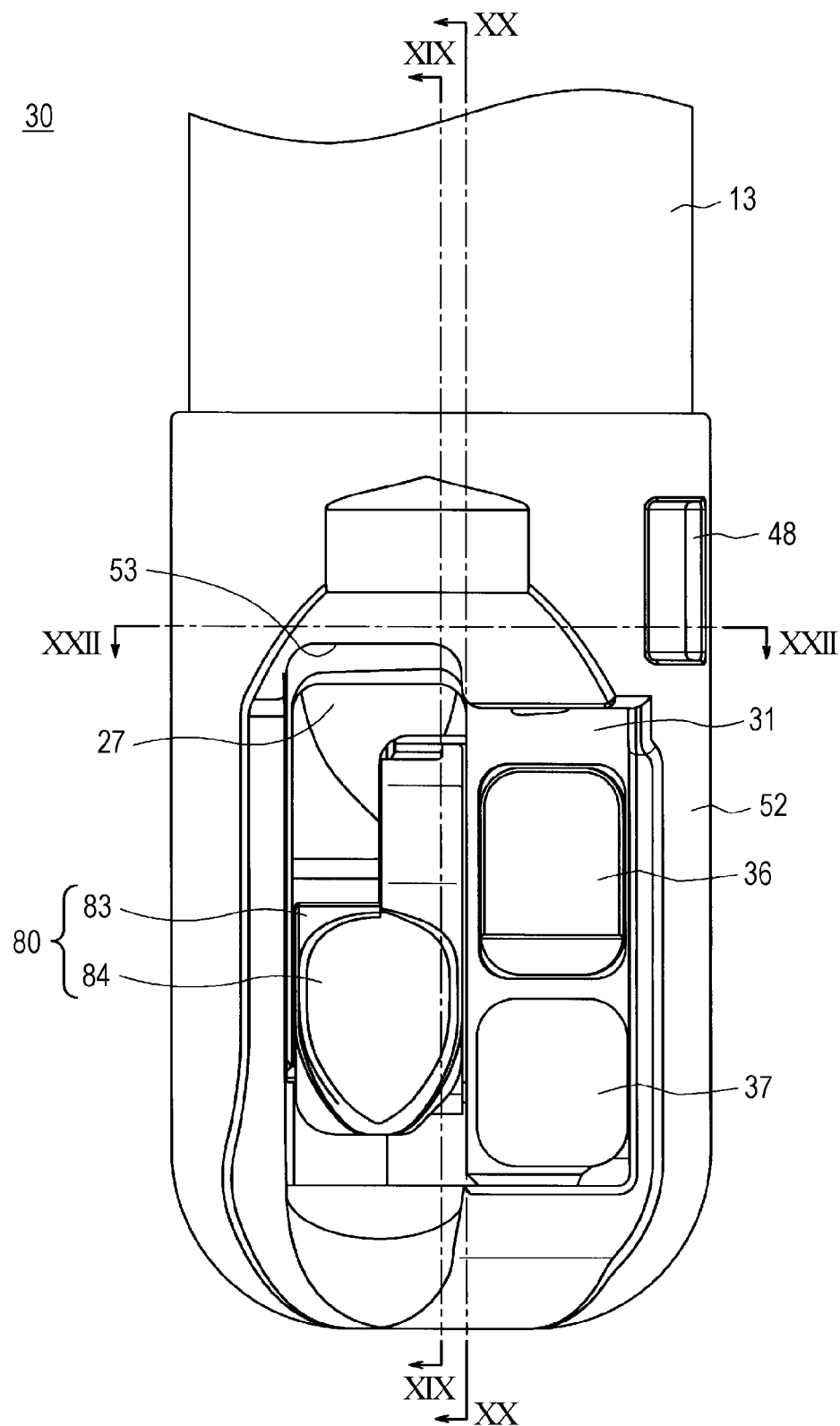
FIG. 4 is a front view of the distal tip of the insertion portion.

FIG. 4 is a front view of the distal tip of the insertion portion 30. The cover 52 has a rectangular concave portion 48 in the vicinity of an opening end portion 56. Each side of the concave portion 48 falls substantially vertically from the surface of the cover 52. The concave portion 48 is thinner than other portions of the cover 52 in the circumferential direction, and is a portion that is easily flexed when an external force is applied thereto by being pushed by a finger or the like. The concave portion 48 is an example of a flexible portion of this embodiment.

The endoscope cap 50 and the elevator 80 can be attached to and detached from the endoscope 10 according to this embodiment through the insertion portion 30. The endoscope cap 50 has the cover 52 that is an exterior member. Detailed configurations of the endoscope cap 50 and the elevator 80 will be described later.

Figure 5:
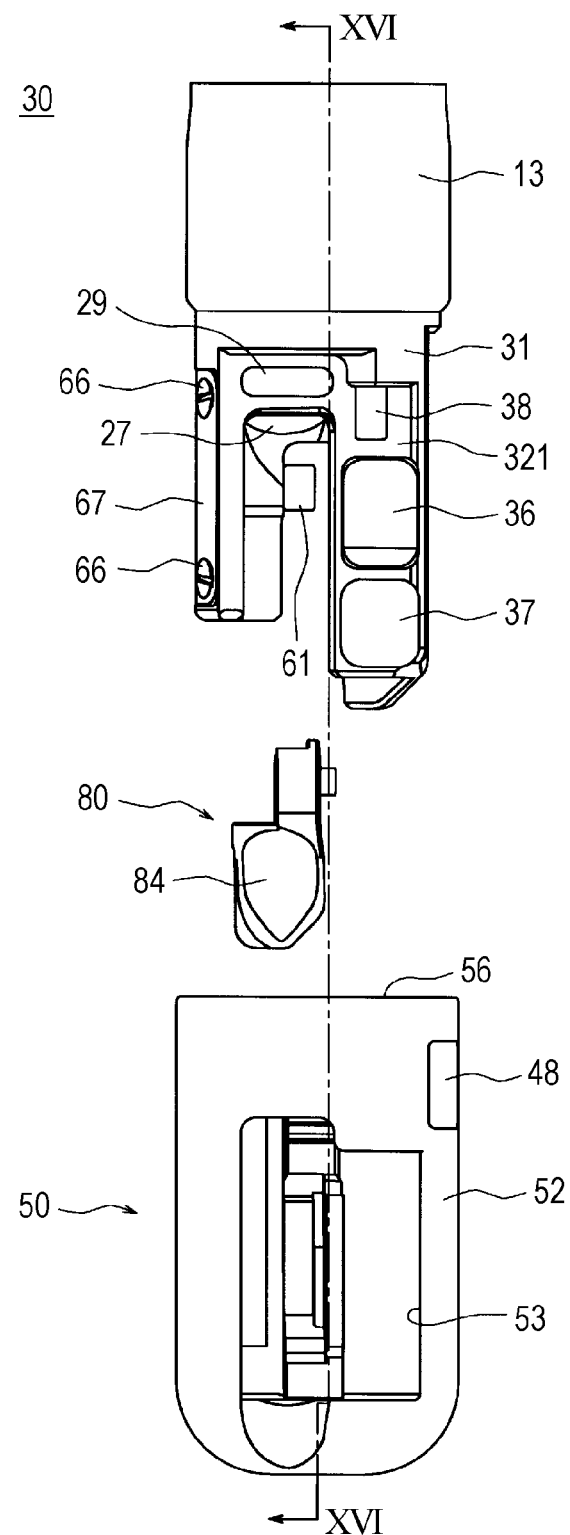
FIG. 5 is a front view for describing a state where an endoscope cap and an elevator are dismounted from the distal tip of the insertion portion.
Figure 6:
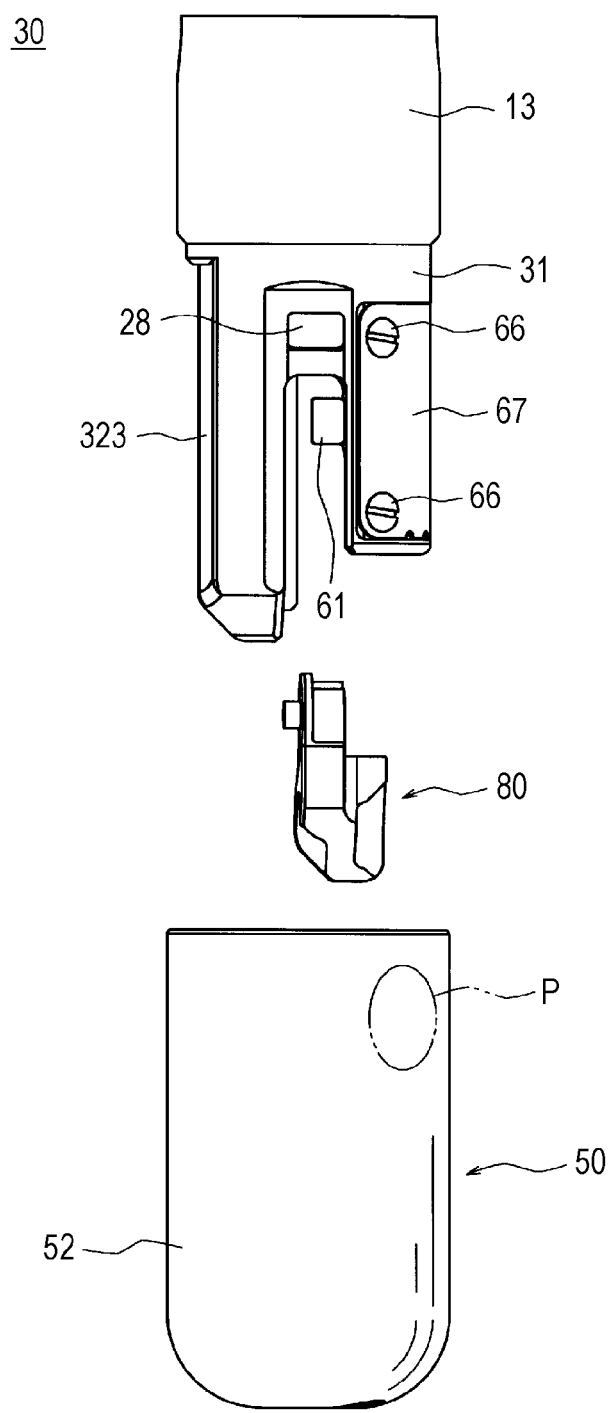
FIG. 6 is a back view for describing the state where the endoscope cap and the elevator are dismounted from the distal tip of the insertion portion.

FIG. 5 is a front view for describing a state where the endoscope cap 50 and the elevator 80 are dismounted from the distal tip of the insertion portion 30. FIG. 6 is a back view illustrating a state where the endoscope cap 50 and the elevator 80 are dismounted from the distal tip of the insertion portion 30.

A user holds the bending section 13 with one hand and picks the cover 52 with two fingers of the other hand. At this time, when one of the two fingers pushes the concave portion 48, the other finger naturally pushes a region indicated by P in FIG. 6. The user can remove the endoscope cap 50 from the insertion portion 30 as will be described later by pressing the cover 52 with the two fingers to slightly deform the cover 52 and then pull the cover 52 to the distal tip side. At this time, the elevator 80 also comes off the insertion portion 30 together with the endoscope cap 50.

Figure 7:
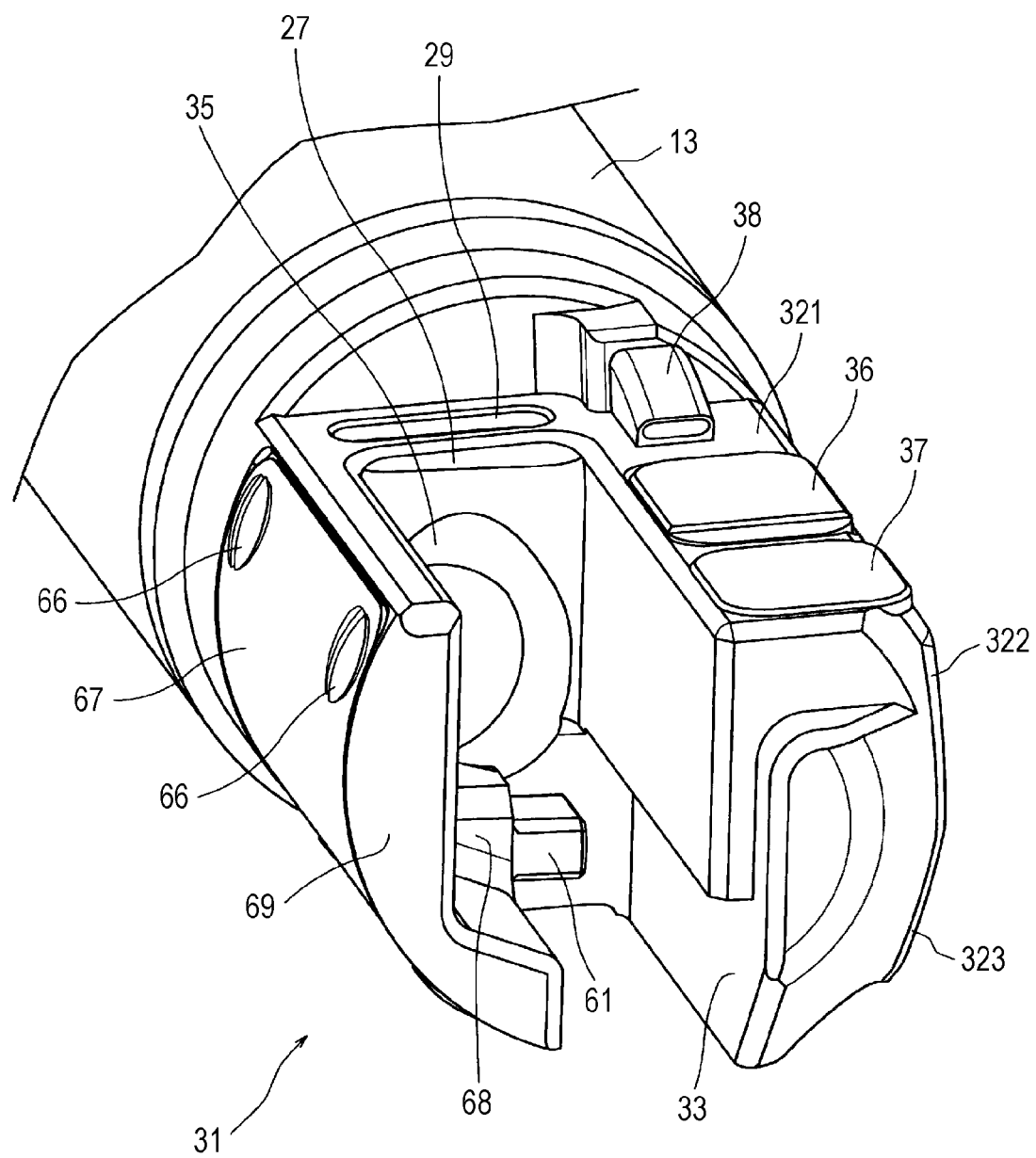
FIG. 7 is a perspective view of the distal tip of the insertion portion with the endoscope cap and the elevator dismounted.

FIG. 7 is a perspective view of the distal tip of the insertion portion 30 from which the endoscope cap 50 and the elevator 80 are dismounted. The configuration of the distal tip of the insertion portion 30 will be described with reference to FIGS. 5 to 7. The distal tip 31 has a substantially cylindrical shape and is divided into an optical housing portion 33 and a lever chamber 69 by a groove provided from the distal tip side toward the operation unit side at a position deviated from the center. The channel outlet 35 is open to a bottom of the groove. A curved portion 27 is provided in the vicinity of the channel outlet 35. A shape of the curved portion 27 will be described later.

The distal tip 31 has a first flat surface portion 321 formed by cutting a part of a circumferential surface thereof into a flat shape. A third engagement portion 29 is provided on a portion of the first flat surface portion 321 along the bottom of the groove separating the optical housing portion 33 from the lever chamber 69. The third engagement portion 29 is an oval recess. The distal tip 31 has a fourth engagement portion 28 (see FIG. 6) on the back side of the third engagement portion 29. The fourth engagement portion 28 is a rectangular recess.

The observation window 36 and the illumination window 37 are arranged on a side of the optical housing portion 33 of the first flat surface portion 321. A nozzle 38 that sprays water and air to the observation window 36 to clean the observation window 36 is provided on the operation unit side of the observation window 36.

The lever chamber 69 is hollow and is covered with a rectangular thin plate-shaped lever chamber lid 67 along an outer circumferential surface of the distal tip 31. The lever chamber lid 67 is fixed at four corners using lid screws 66. The lid screw 66 is an example of a fixing member of this embodiment. The lever chamber 69 has a support wall 68 on the optical housing portion 33 side. The elevator base connection portion 61 protrudes from the support wall 68 toward the optical housing portion 33. The elevator base connection portion 61 is an axis having a rectangular cross section. The elevator base connection portion 61 will be described later.

Figure 8:
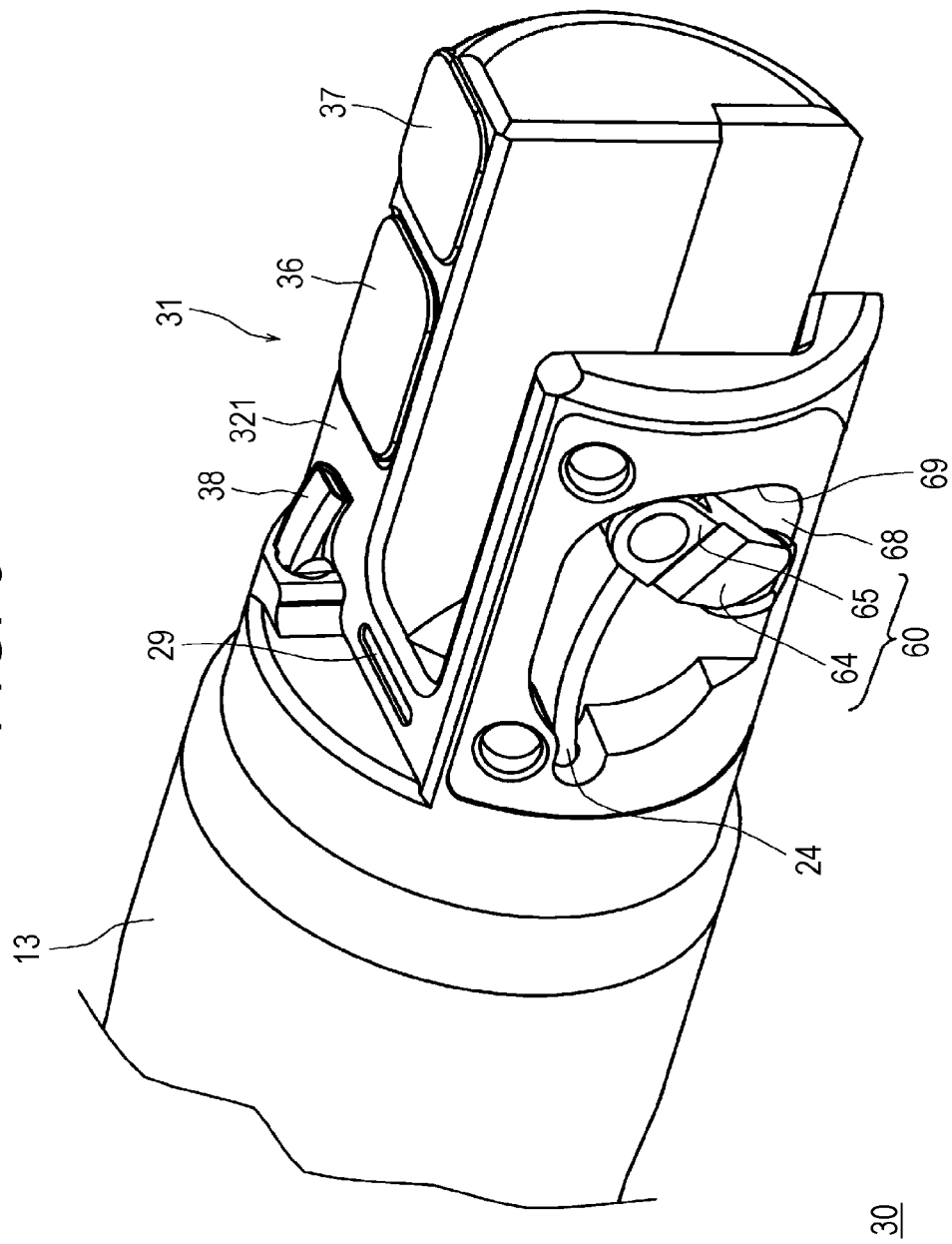
FIG. 8 is a perspective view of the distal tip of the insertion portion with the endoscope cap, the elevator, and a lever chamber lid dismounted.

FIG. 8 is a perspective view of the distal tip of the insertion portion 30 from which the endoscope cap 50, the elevator 80, and the lever chamber lid 67 are dismounted. The lever 60 is provided inside the lever chamber 69. The lever 60 has a wire fixing portion 65 at one end and a lever shaft 63 (see FIG. 17) and the elevator base connection portion 61 at the other end as will be described later. The lever 60 is rotatably supported by a hole provided in the support wall 68.

The wire fixing portion 65 is connected to an end portion of an elevation wire 24. The elevation wire 24 is connected to the elevation operation lever 21 (see FIG. 1) through the insertion portion 30. More specifically, the elevation wire 24 is inserted through a guide pipe (not illustrated) having an inner diameter slightly larger than an outer diameter of the elevation wire 24. The guide pipe (not illustrated) passes through the insertion portion 30 in a longitudinal direction. Thus, a distal tip of the elevation wire 24 moves forward and backward in conjunction with the operation of the elevation operation lever 21.

The lever 60 is rotated about the lever shaft 63 by being pushed and pulled by the distal tip of the elevation wire 24. The elevation wire 24 is an example of a rotating portion of this embodiment. The elevation wire 24 is remotely operated by the elevation operation lever 21.

Figure 9:
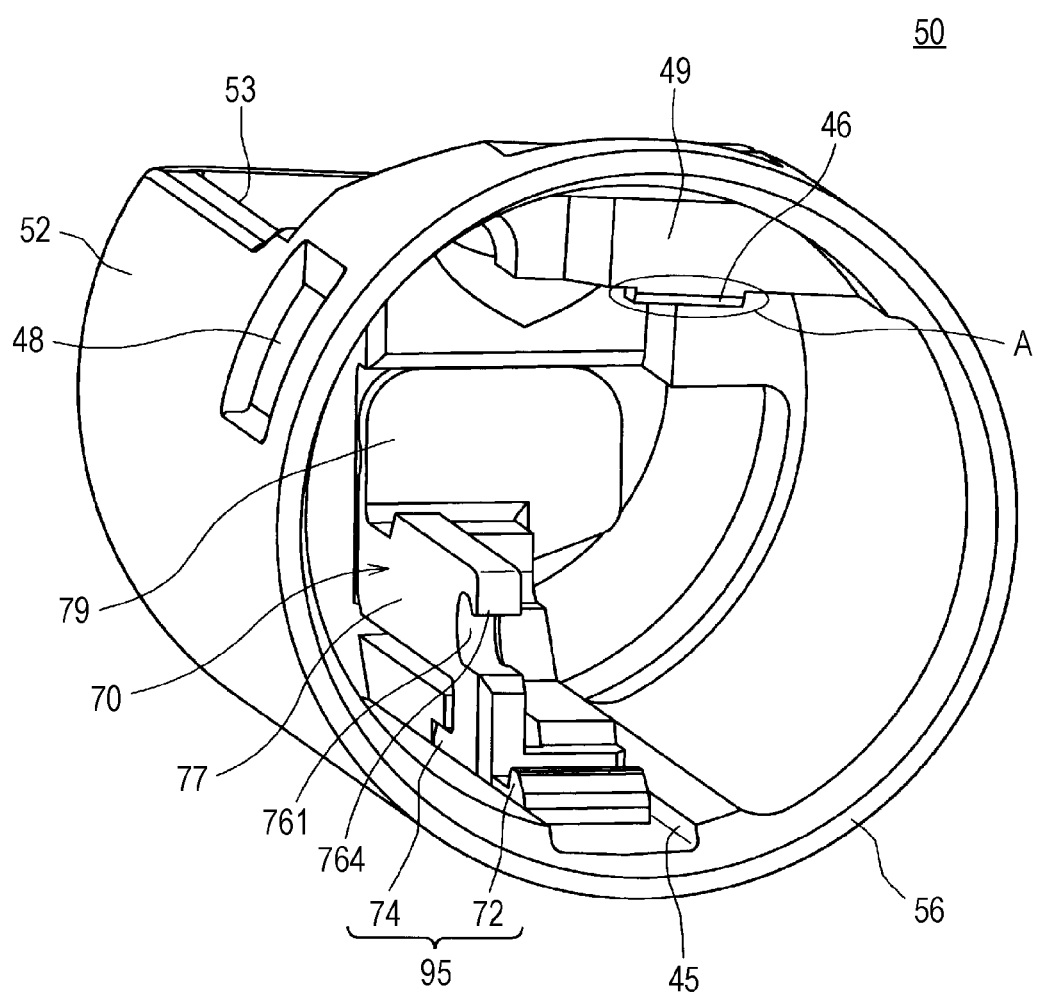
FIG. 9 is a perspective view of the endoscope cap as viewed from an attachment side with respect to the endoscope.
Figure 10:
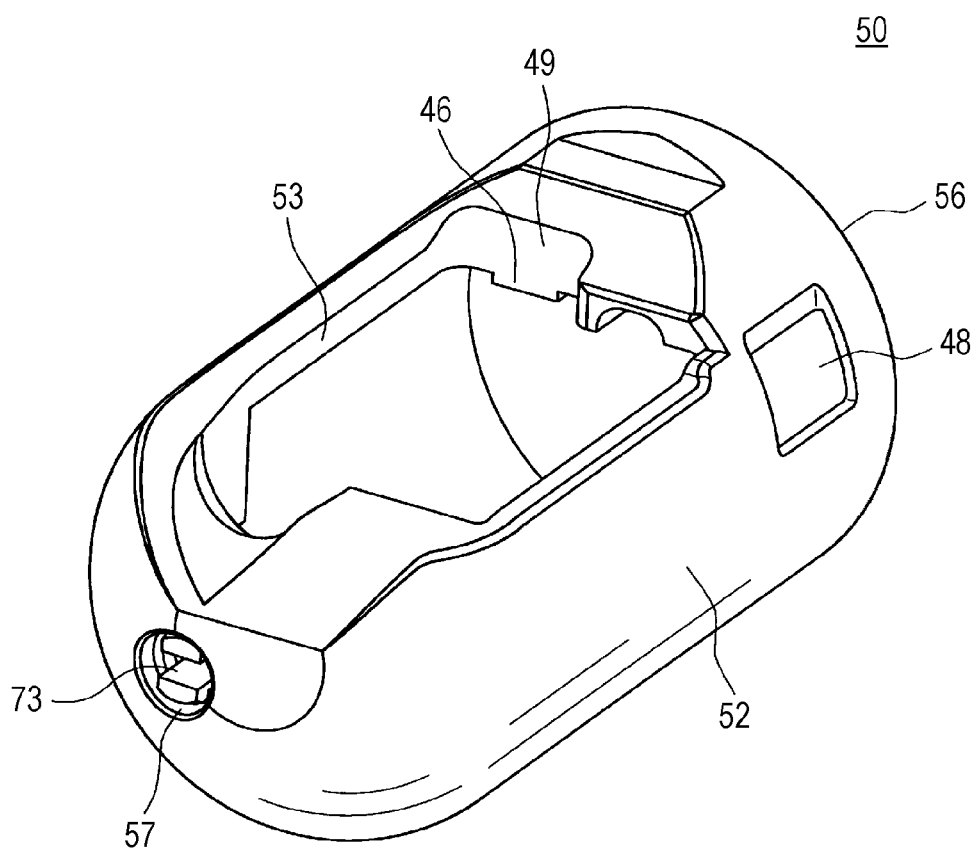
FIG. 10 is a perspective view of the endoscope cap as viewed from a bottom side of a cover.

FIG. 9 is a perspective view of the endoscope cap 50 as viewed from an attachment side with respect to the endoscope 10. FIG. 10 is a perspective view of the endoscope cap 50 as viewed from the bottom side of the cover 52. The endoscope cap 50 has a cover 52 and a pedestal 70. The cover 52 is of a bottomed tube type having an opening at one end. As described above, the opening at one end of the cover 52 is referred to as the opening end portion 56.

As described above, the cover 52 has the window portion 53 in a tubular portion. The window portion 53 is open over substantially the entire length at one place on the circumferential surface of the cover 52. The cover 52 has a pedestal groove 45 extending from the opening end portion 56 toward the bottom, on an inner surface facing the window portion 53. The pedestal 70 is fixed to the pedestal groove 45. The pedestal 70 will be described later.

The cover 52 has a plate-shaped protruding portion 49 that protrudes inward along an edge on the opening end portion 56 side of the window portion 53. A first engagement portion 46 is provided on a part of the distal tip of the protruding portion 49 so as to protrude inward.

Figure 11:
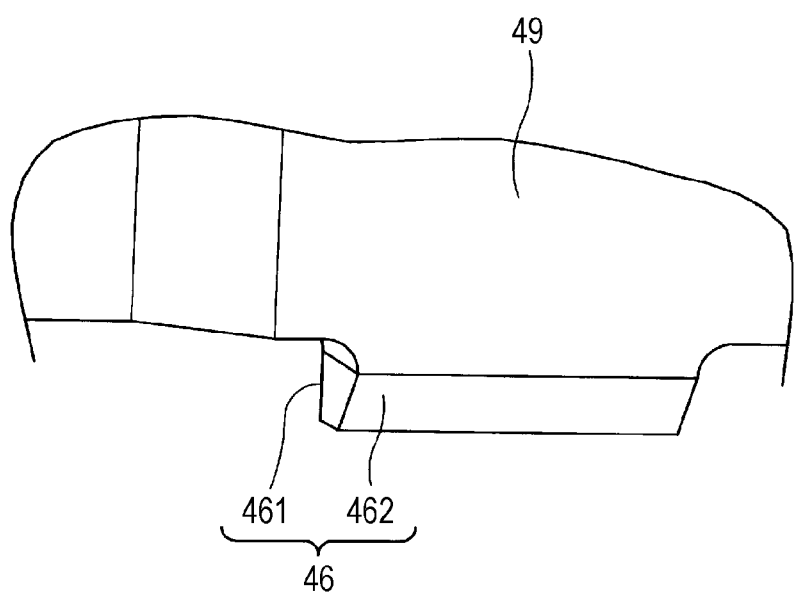
FIG. 11 is an enlarged perspective view of a first engagement portion.

FIG. 11 is an enlarged perspective view of the first engagement portion 46. FIG. 11 is an enlarged view of part A in FIG. 9. A shape of the first engagement portion 46 will be described with reference to FIGS. 9 to 11. The first engagement portion 46 has a first wedge surface 461 on a bottom side and a second wedge surface 462 on the opening end portion 56 side. The first wedge surface 461 is a flat surface which is continuous with a surface of the protruding portion 49 on the bottom side and extends along an edge of the window portion 53.

The second wedge surface 462 is a flat surface which is inclined with respect to an axial direction of the tubular portion having the inside on the bottom side and the outside on the opening end portion 56 side. When the first engagement portion 46 is cut by a surface parallel to the axis of the tubular portion, the first wedge surface 461 and the second wedge surface 462 are formed into a wedge shape.

Figure 12:
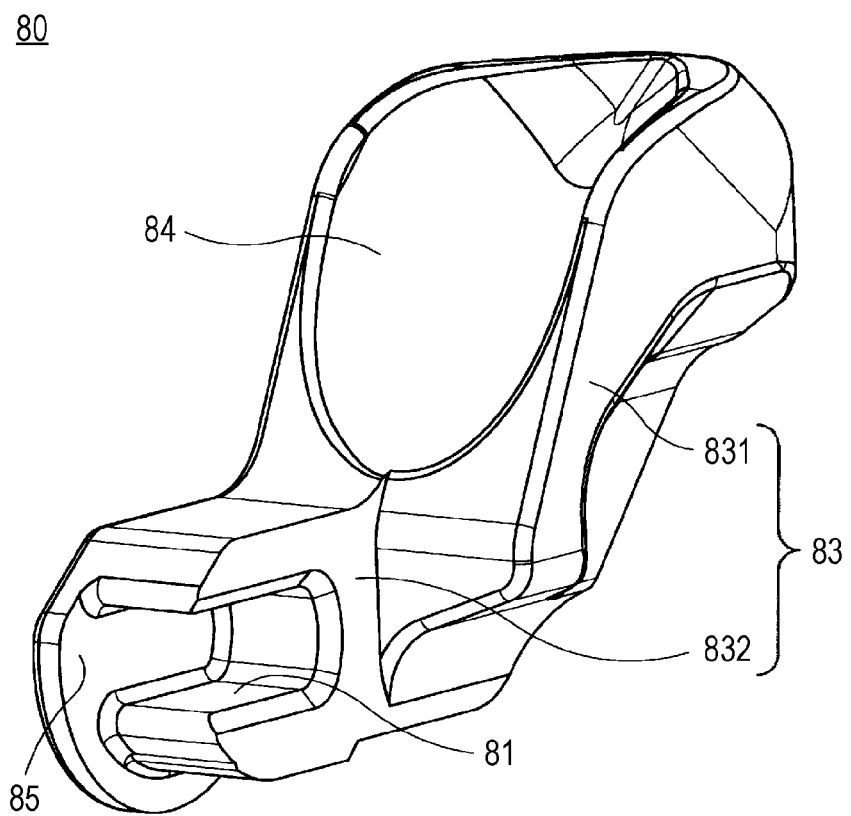
FIG. 12 is a perspective view of the elevator.
Figure 13:
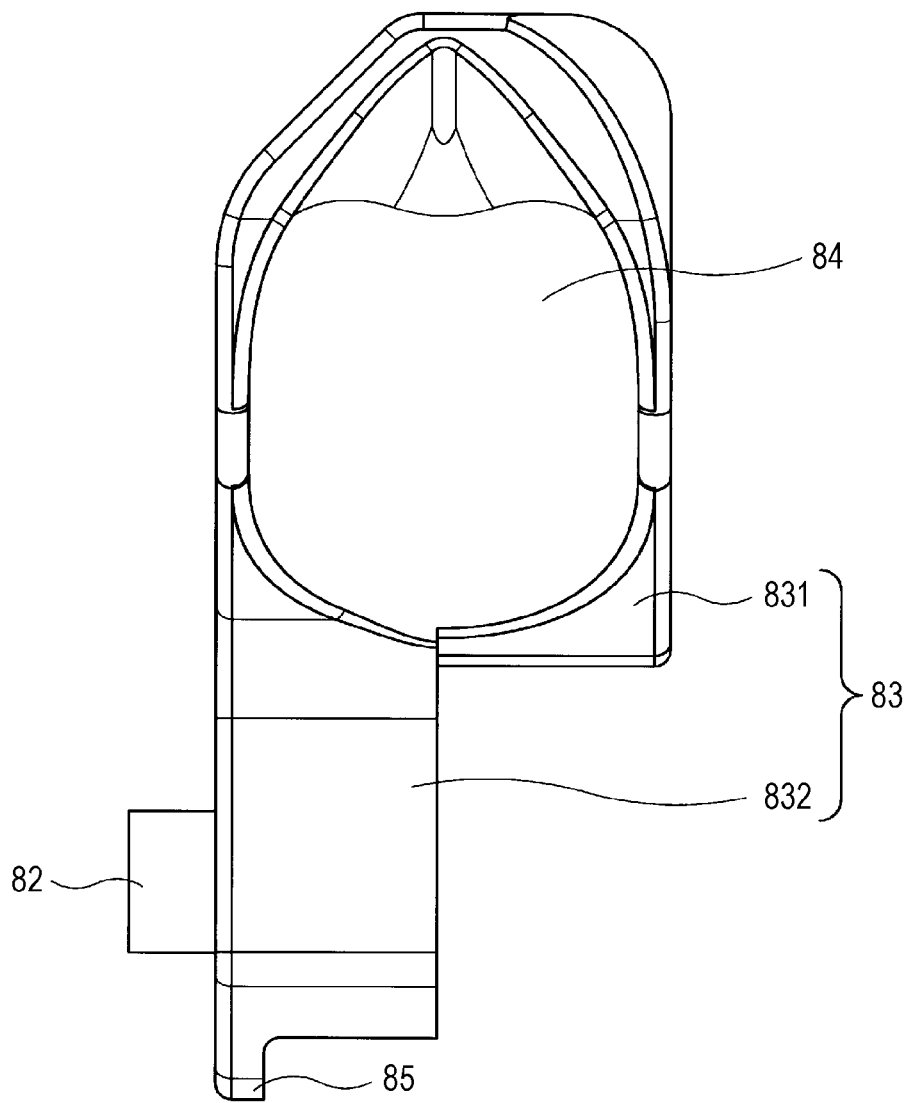
FIG. 13 is a front view of the elevator.
Figure 14:
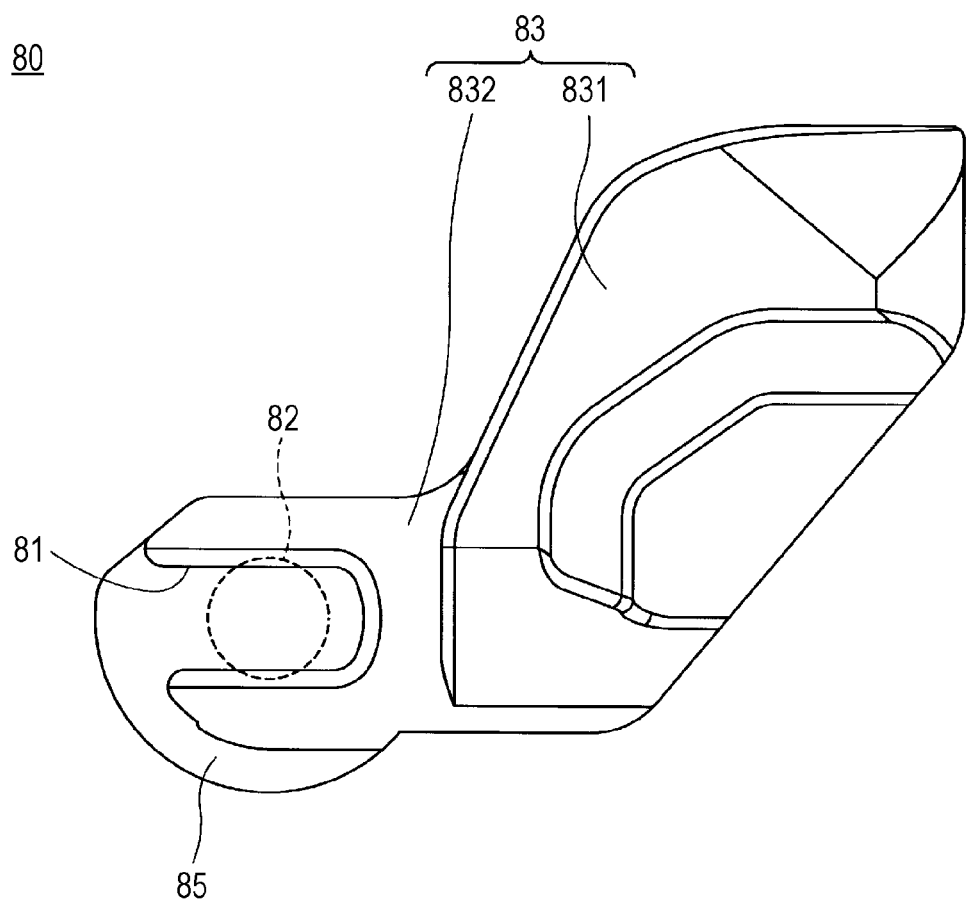
FIG. 14 is a side view of the elevator.

FIG. 12 is a perspective view of the elevator 80. FIG. 13 is a front view of the elevator 80. FIG. 14 is a side view of the elevator 80. The configuration of the elevator 80 will be described with reference to FIGS. 12 to 14.

The elevator 80 has a substantially L-shaped elevation portion 83. The elevation portion 83 has a first elevation portion 831 having a spoon-shaped recessed portion 84 on one surface thereof and a second elevation portion 832 protruding to the same side as a surface having the recessed portion 84 of the first elevation portion 831 from an end of the first elevation portion 831.

A lever connection portion 81 is provided at an end portion of the second elevation portion 832. The lever connection portion 81 is a U-shaped groove which is open toward the end portion of the second elevation portion 832. One side of the lever connection portion 81 is covered with a plate-shaped flange 85. An elevator shaft 82 protrudes from a surface opposite to the flange 85.

That is, the elevator shaft 82 protrudes from one surface of the flange 85, and the elevation portion 83 protrudes from the other surface of the flange 85 in a direction intersecting the central axis of the elevator shaft 82. The lever connection portion 81 is provided on a proximal end portion side of the elevation portion 83.

The lever connection portion 81 is arranged so as to sandwich the central axis of the elevator shaft 82 as indicated by the broken line in FIG. 14.

Figure 15:
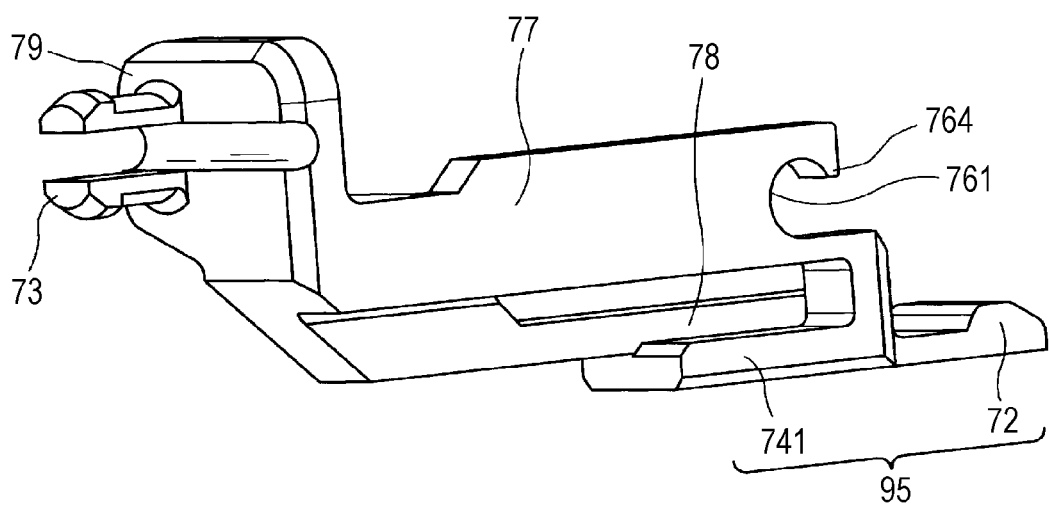
FIG. 15 is a perspective view of a pedestal.

FIG. 15 is a perspective view of the pedestal 70. A configuration of the pedestal 70 will be described with reference to FIG. 15. The pedestal 70 has a rectangular plate-shaped base portion 95 and a substantially rectangular plate-shaped first wall 77 extending from a support leg rising from a center portion in the longitudinal direction of the base portion 95 along the longitudinal direction of the base portion 95. Further, a substantially rectangular plate-shaped second wall 78 rises from the base portion 95 in parallel to the first wall 77. The first wall 77 and the second wall 78 are separated from each other in a width direction of the base portion 95.

A rectangular plate-shaped third wall 79 that straddles the first wall 77 and the second wall 78 is connected to an end portion of the first wall 77. The third wall 79 is provided with a first fixing protrusion 73 on a surface opposite to the first wall 77. The first fixing protrusion 73 is a cylindrical protrusion having a split groove. The first fixing protrusion 73 has a retainer which is slightly thick at an end portion thereof.

The base portion 95 has a thick plate portion 741 which is thicker than other portions on the third wall 79 side in the longitudinal direction and on the first wall 77 side in the width direction. The distal tip of the thick plate portion 741 is chamfered. The base portion 95 has a second engagement portion 72 at the end portion opposite to the third wall 79, which rises in a substantially semicircular shape over the entire width. The width of the base portion 95 corresponds to the pedestal groove 45.

The first wall 77 has an elevator mounting groove 761. The elevator mounting groove 761 is an approximately U-shaped groove that has an opening at the end portion on the root side of the first wall 77 and extends parallel to the base portion 95.

The elevator mounting groove 761 is provided with an elevator pivot portion 764 protruding inward at an edge of the opening remote from the base portion 95. A gap between the inner surface of the elevator mounting groove 761 on the base portion 95 side and the distal tip of the elevator pivot portion 764 forms an inlet to the bottom of the elevator mounting groove 761. The elevator mounting groove 761 is an example of an elevator support portion of this embodiment.

Further, the elevator pivot portion 764 may be provided on the base portion 95 side of the opening. The elevator pivot portion 764 may be provided so as to be opposed from both sides.

Figure 16:
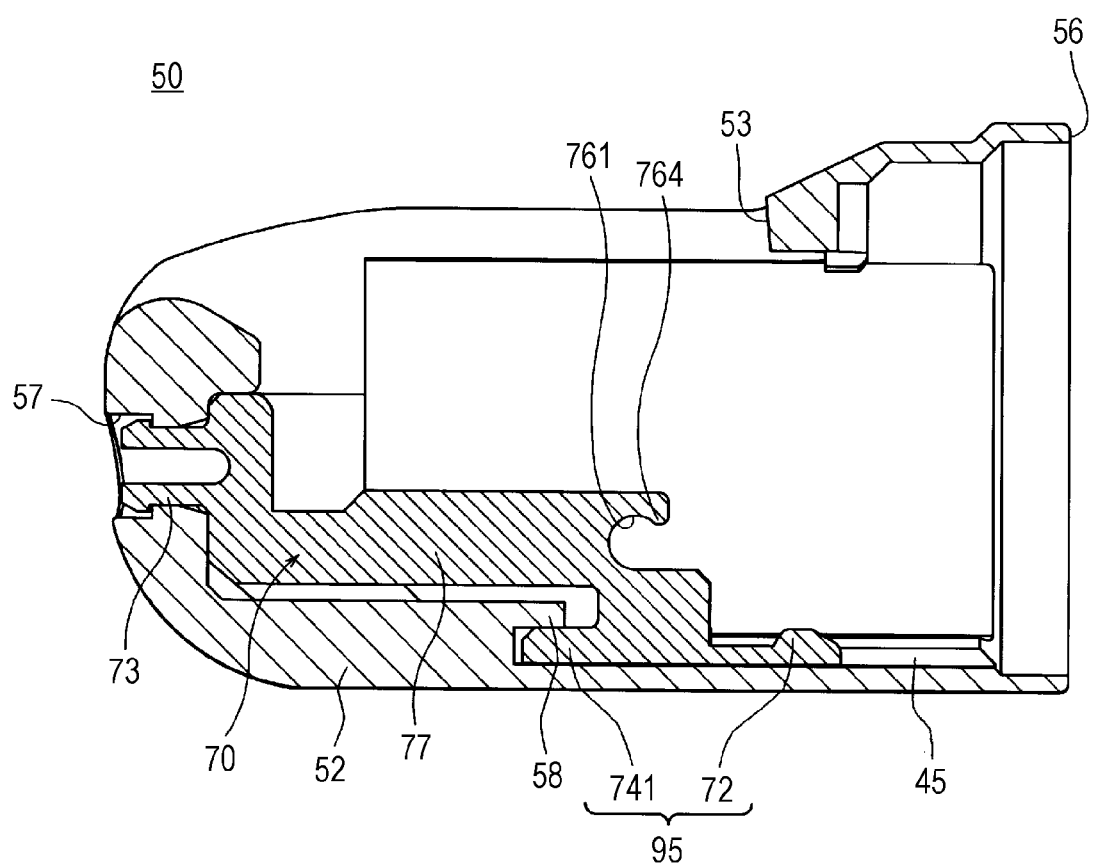
FIG. 16 is a cross-sectional view of the endoscope cap taken along line XVI-XVI of FIG. 5.

FIG. 16 is a cross-sectional view of the endoscope cap 50 taken along line XVI-XVI of FIG. 5. A XVI-XVI cross section is a cross section cutting the first wall 77 in a thickness direction along the longitudinal direction of the insertion portion 30. A configuration of the endoscope cap 50 will be described with reference to FIGS. 9 to 11, 15, and 16.

At the bottom of the cover 52, a pedestal fixing hole 57 is provided. The pedestal fixing hole 57 is a stepped through hole having a large diameter portion on the outer surface side of the cover 52. The small diameter portion of the pedestal fixing hole 57 has a tapered shape expanding toward the inner surface of the cover 52. The inner diameter of the pedestal fixing hole 57 corresponds to the outer diameter of the first fixing protrusion 73.

The cover 52 has a second fixing protrusion 58 on the inner surface. The second fixing protrusion 58 is a protrusion protruding from the end of the pedestal groove 45 toward the opening end portion 56 side. The distance between the second fixing protrusion 58 and the bottom of the pedestal groove 45 corresponds to the thickness of the thick plate portion 741.

An outline of a method for assembling the endoscope cap 50 will be described. With the first fixing protrusion 73 side of the pedestal 70 first, the base portion 95 and the pedestal groove 45 of the cover 52 are aligned in the circumferential direction. The pedestal 70 is pushed into the cover 52.

The first fixing protrusion 73 is elastically deformed and passes through the small diameter portion of the pedestal fixing hole 57. After the retainer of the first fixing protrusion 73 has passed through the small diameter portion of the pedestal fixing hole 57, the first fixing protrusion 73 elastically returns. The second fixing protrusion 58 and the thick plate portion 741 engage. As described above, the pedestal 70 and the cover 52 are fixed. Further, an adhesive may be applied to the pedestal groove 45 and the like, and the pedestal 70 and the cover 52 may be bonded and fixed.

Figure 17:
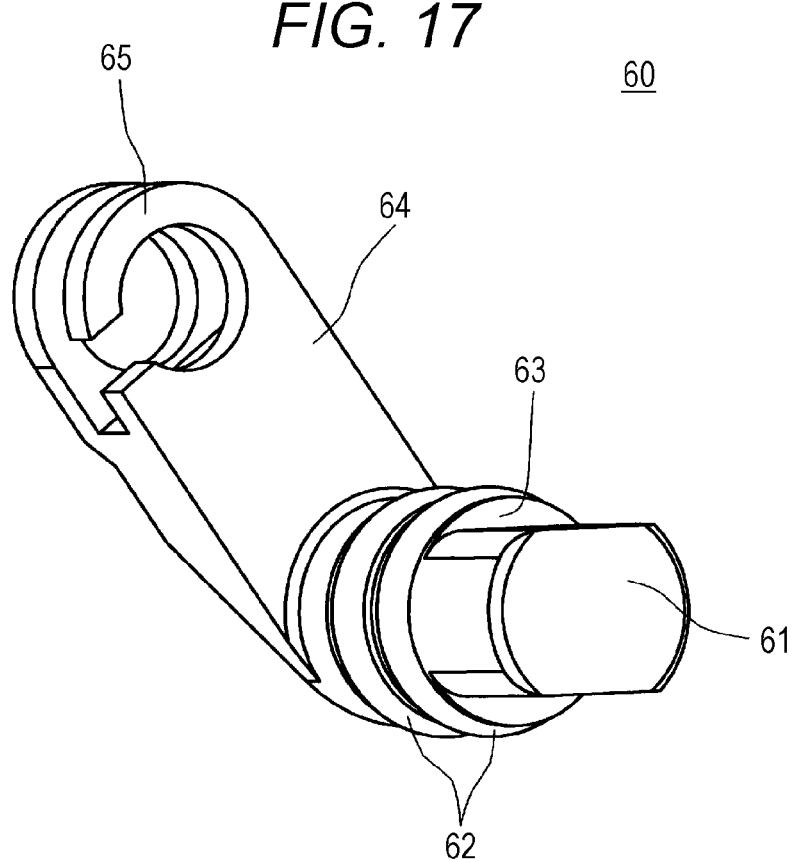
FIG. 17 is a perspective view of the lever.

FIG. 17 is a perspective view of the lever 60. The lever 60 has the lever shaft 63 at one end and the wire fixing portion 65 at the other end. The elevator base connection portion 61, which is the axis of the rectangular cross section, protrudes from one end surface of the lever shaft 63 in the same direction as the central axis of the lever shaft 63. In the following description, a plate-shaped portion connecting the lever shaft 63 and the wire fixing portion 65 is referred to as a rotating connection portion 64. The rotating connection portion 64 protrudes from the end portion of the lever shaft 63 on the opposite side of the elevator base connection portion 61 in a direction intersecting the central axis of the lever shaft 63. The rotating connection portion 64 rotates within the lever chamber 69 as illustrated in FIG. 8.

Two O-rings 62 are mounted to the lever shaft 63. Returning to FIG. 7, the description will be continued. The lever shaft 63 is inserted into a hole provided in the support wall 68 from the lever chamber 69 side, and the lever 60 is rotatably supported in a state where the elevator base connection portion 61 faces the optical housing portion 33. The hollow lever chamber 69 is water-tightly sealed by the O-ring 62 and the lever chamber lid 67.

Figure 18:
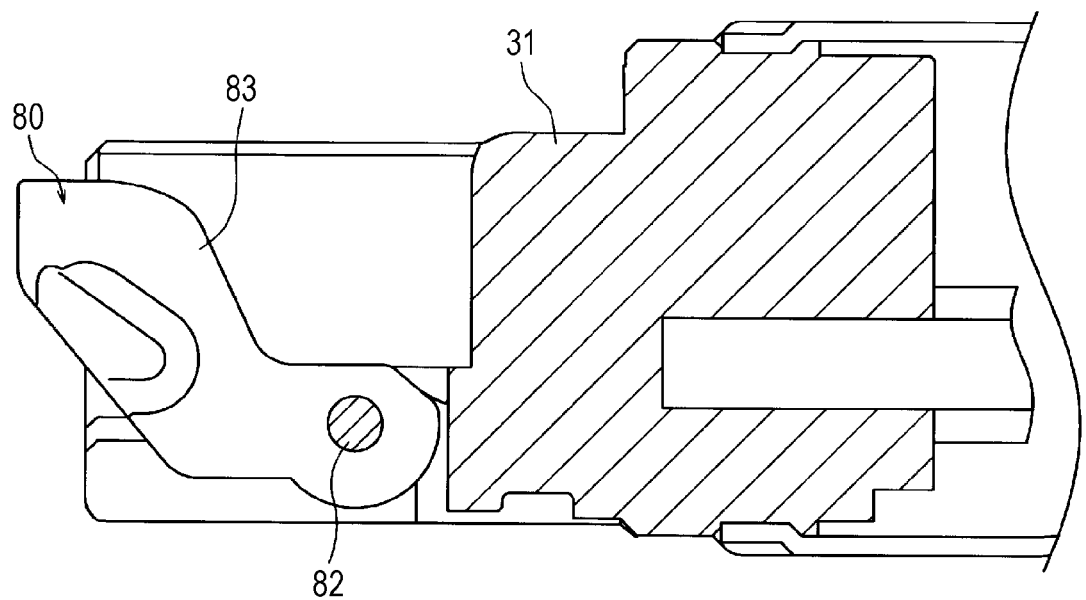
FIG. 18 is a cross-sectional view of the distal tip of the insertion portion from which the endoscope cap is dismounted.

FIG. 18 is a cross-sectional view of the distal tip of the insertion portion 30 from which the endoscope cap 50 is dismounted. FIG. 18 is a cross section taken along the line XVI-XVI of FIG. 5, similar to FIG. 16, and illustrates a state in which the elevator 80 is mounted to the distal tip of the insertion portion 30.

The elevator base connection portion 61 described with reference to FIG. 7 is engaged with the lever connection portion 81 described with reference to FIG. 12. The endoscope cap 50 described with reference to FIG. 16 is placed and fixed on the elevator 80 and the distal tip 31 from the left side in FIG. 18.

Figure 19:
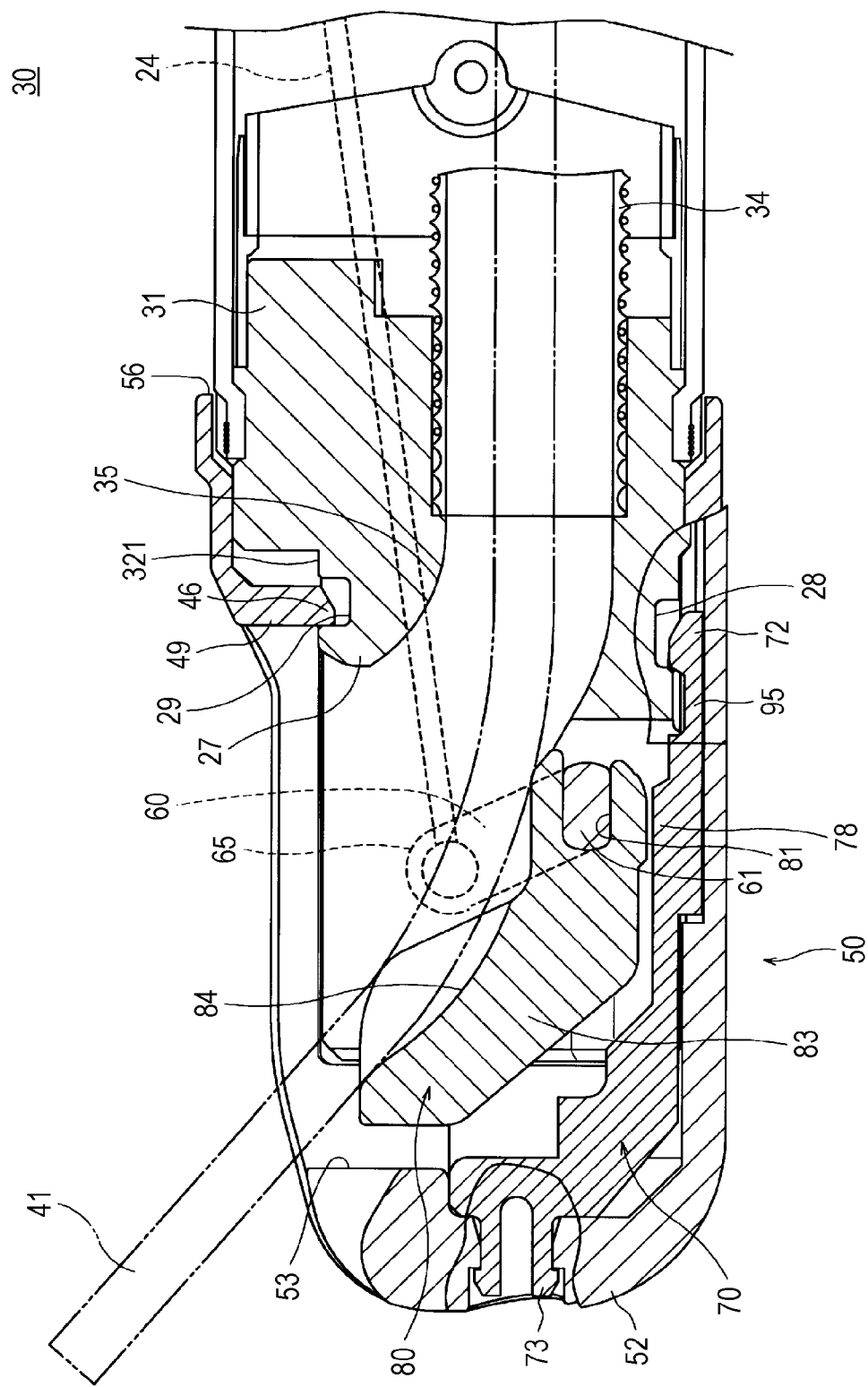
FIG. 19 is a cross-sectional view of the insertion portion taken along line XIX-XIX of FIG. 4.
Figure 20:
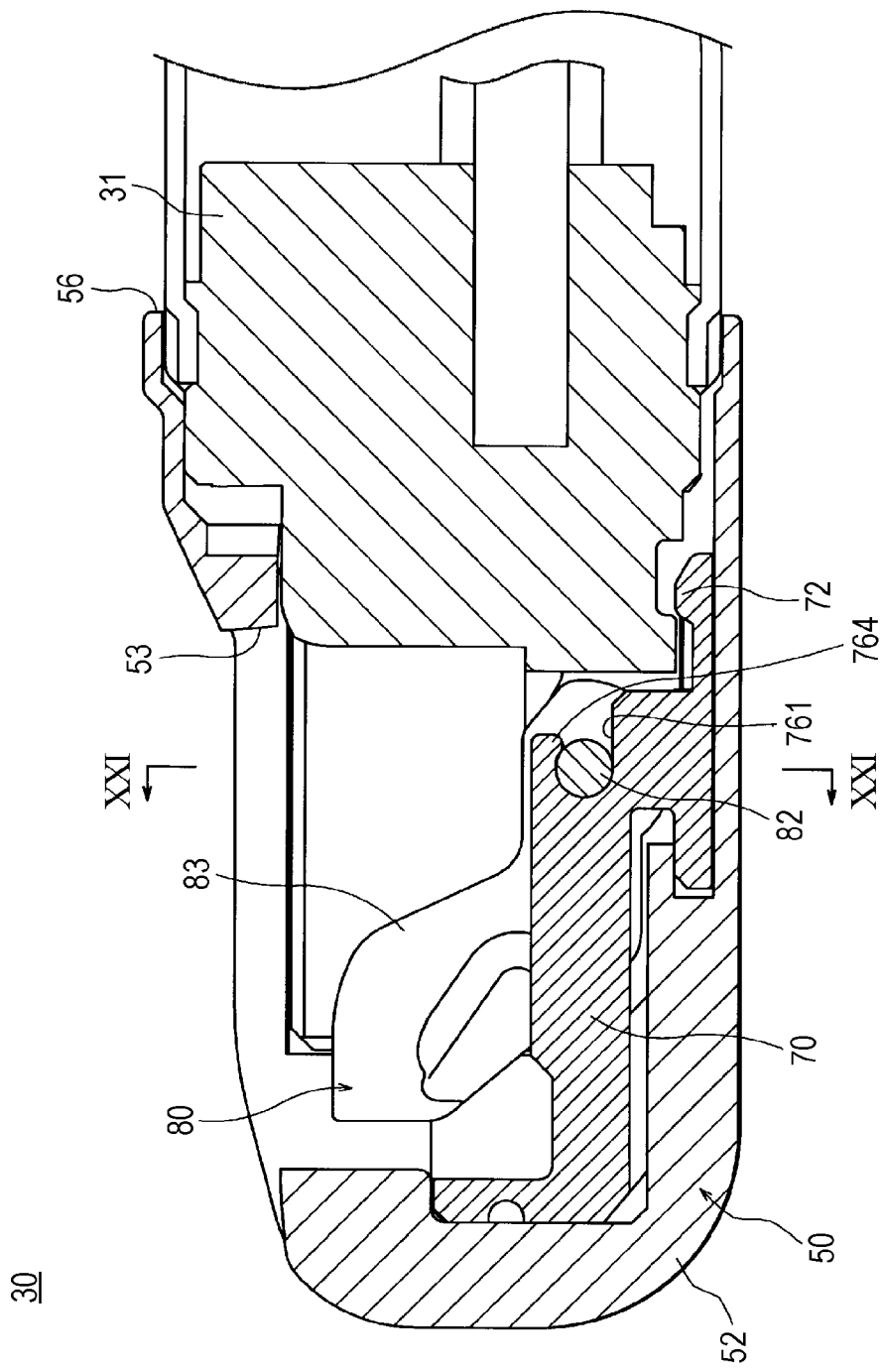
FIG. 20 is a cross-sectional view of the insertion portion taken along line XX-XX of FIG. 4.
Figure 21:
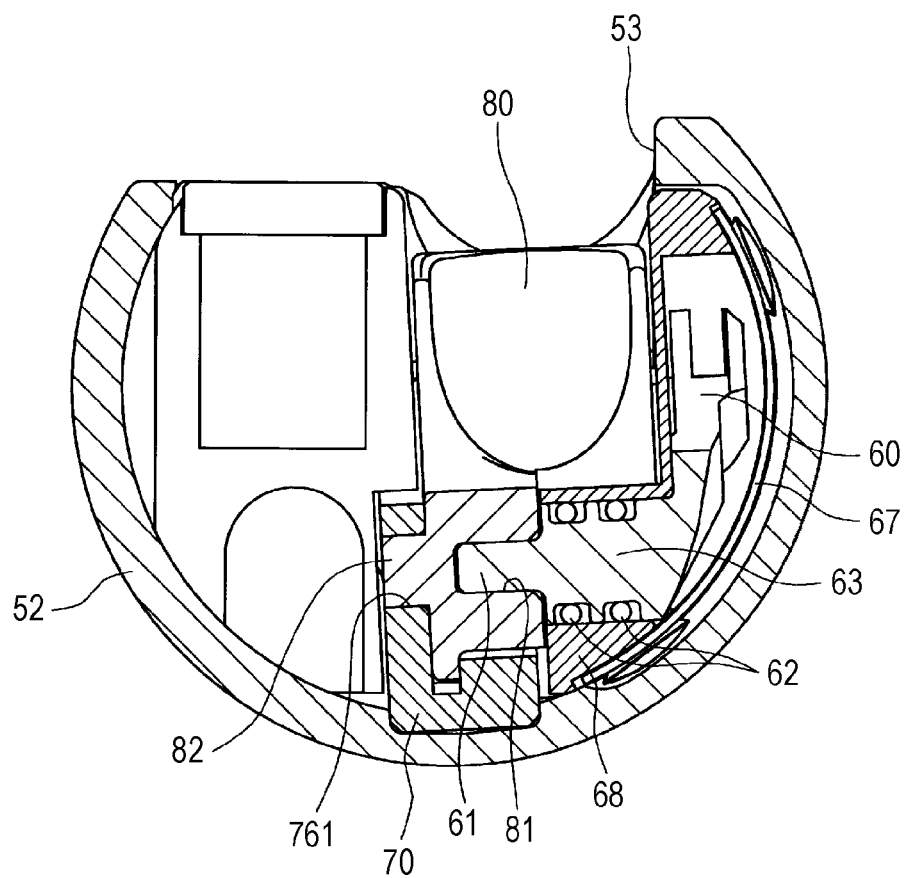
FIG. 21 is a cross-sectional view of the insertion portion taken along line XXI-XXI of FIG. 20.

FIG. 19 is a cross-sectional view of the insertion portion 30 taken along line XIX-XIX of FIG. 4. A XIX-XIX cross section is a cross section cutting the insertion portion 30 in the longitudinal direction at a position of the elevator base connection portion 61. FIG. 20 is a cross-sectional view of the insertion portion 30 taken along line XX-XX of FIG. 4. A XX-XX cross section is a cross section cutting the insertion portion 30 in the longitudinal direction at a position of the elevator shaft 82. FIG. 21 is a cross-sectional view of the insertion portion 30 taken along line XXI-XXI of FIG. 20. A XXI-XXI cross section is a cross section cut perpendicularly to the longitudinal direction of the insertion portion 30 at the position of the elevator shaft 82. A configuration in which the elevator 80 and the endoscope cap 50 are fixed to the distal tip of the insertion portion 30 will be described with reference to FIGS. 19 to 21.

The endoscope cap 50 has the opening end portion 56 facing the distal tip 31 side. As illustrated in FIG. 19, the first engagement portion 46 on the inner surface of the endoscope cap 50 is engaged with the third engagement portion 29 on the distal tip 31. In the engagement portion, the first wedge surface 461 abuts on a surface of the third engagement portion 29 on the operation unit side.

Similarly, the second engagement portion 72 on the inner surface of the endoscope cap 50 is engaged with the fourth engagement portion 28 on the distal tip 31. The endoscope cap 50 is fixed to the distal tip 31 as the endoscope cap 50 is engaged with the distal tip 31 at two opposing places on the inner surface.

The elevator base connection portion 61, which is the axis of the rectangular cross section, is inserted into the lever connection portion 81 of the U-shaped groove type. As a result, the lever 60 is engaged with the elevator 80.

As illustrated in FIG. 20, the elevator mounting groove 761 and the elevator shaft 82 engage. The elevator 80 is supported at both ends by the elevator mounting groove 761 and the elevator base connection portion 61. As illustrated in FIG. 21, the lever shaft 63 and the elevator shaft 82 are coaxial. The elevator 80 smoothly rotates around the lever shaft 63 and the elevator shaft 82.

Figure 22:
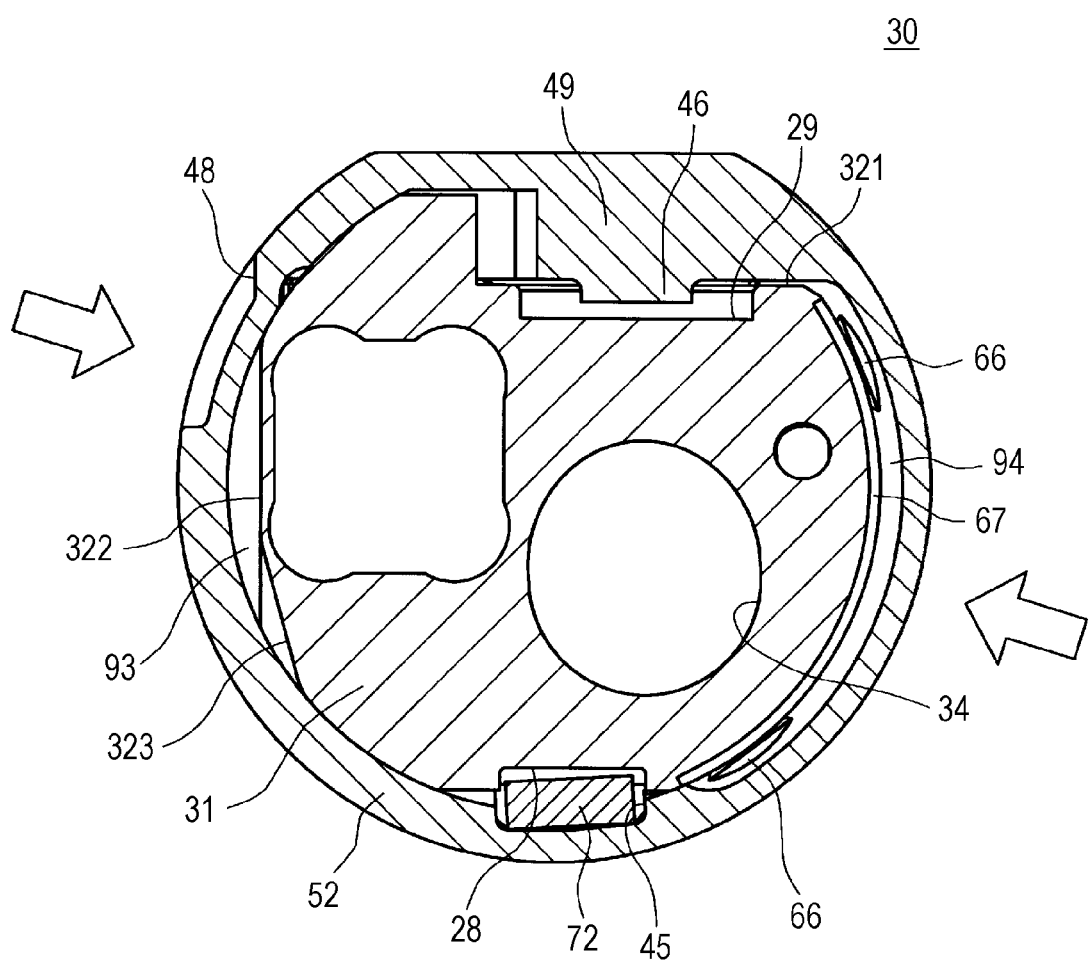
FIG. 22 is a cross-sectional view of the insertion portion taken along line XXII-XXII of FIG. 4.

FIG. 22 is a cross-sectional view of the insertion portion 30 taken along line XXII-XXII of FIG. 4. A second flat surface portion 322 and a third flat surface portion 323, formed by flatly cutting a part of the circumferential surface of the distal tip 31, are formed on the outer side of the optical housing portion 33. The second flat surface portion 322 and the third flat surface portion 323 are continuous with an angle.

An inner surface of the tubular portion of the cover 52 opposes the second flat surface portion 322 and the third flat surface portion 323 with a space therebetween, thereby forming a first cavity portion 93. The concave portion 48 is arranged at a position corresponding to the first cavity portion 93. The cover 52 is dented on the inner surface of the tubular portion to be thin on the opposite side of the concave portion 48. The inner surface of the thin portion of the cover 52 and the lever chamber lid 67 oppose each other with a space therebetween, thereby forming a second cavity portion 94. A head portion of the lid screw 66 is arranged inside the second cavity portion 94. That is, the second cavity portion 94 is a space for housing the head portion of the lid screw 66 which is a fixing member that fixes the lever chamber lid 67.

When dismounting the endoscope cap 50, the user presses two places of the concave portion 48 and the opposite side thereof with fingers as indicated by the white arrows in FIG. 22. The cover 52 is deformed since the first cavity portion 93 and the second cavity portion 94 exist on the back side of portions to be pressed. Incidentally, the concave portion 48 is thinner than the other portion in the circumferential direction of the cover 52 as described above, and is a flexible portion that is easily flexed by being pushed with the finger or the like.

The user can easily deform the endoscope cap 50 by pressing with a finger. Due to this deformation, the engagement between the first engagement portion 46 and the third engagement portion 29 and the engagement between the second engagement portion 72 and the fourth engagement portion 28 are released.

As the user pulls the endoscope cap 50 to the distal tip side while pressing the endoscope cap 50, the engagement between the lever connection portion 81 and the elevator base connection portion 61 is also released. The user can remove the endoscope cap 50 from the insertion portion 30 with the endoscope cap 50 still connected to the elevator 80.

A procedure for mounting the elevator 80 and the endoscope cap 50 to the distal tip of the insertion portion 30 will be described. The user grips the elevator 80 with a finger or the like. The user adjusts the orientation of the elevator base connection portion 61 and the lever connection portion 81.

The user inserts the elevator 80 from the distal tip side of the insertion portion 30. The elevator base connection portion 61 enters the lever connection portion 81. As described above, the elevator 80 is temporarily stopped to the distal tip of the insertion portion 30.

Further, a slip stopper formed by dimples, shallow grooves, or the like may be provided on the surface of the elevator 80. The work of the user gripping the elevator 80 and mounting it to the distal tip of the insertion portion 30 becomes easy.

Thereafter, the user adjusts the position of the endoscope cap 50 in the circumferential direction with respect to the distal tip 31 using the window portion 53 and the recessed portion 84 as marks. The user pushes the endoscope cap 50 into the distal tip of the insertion portion 30. As illustrated in FIG. 11, the second wedge surface 462 of the first engagement portion 46 is inclined with respect to the longitudinal direction of the tubular portion of the cover 52, and thus, the first engagement portion 46 is hardly caught by the distal tip 31.

The first engagement portion 46 is pushed into the third engagement portion 29 while being elastically deformed. When the first wedge surface 461 enters the third engagement portion 29, the first engagement portion 46 elastically returns and engages with the third engagement portion 29.

As illustrated in FIG. 19, since the second engagement portion 72 is a protrusion that protrudes in a substantially semicircular shape, the second engagement portion 72 is easily pushed into the fourth engagement portion 28. The second engagement portion 72 is also pushed into the fourth engagement portion 28 while being elastically deformed. The second engagement portion 72 is elastically restored when it enters the fourth engagement portion 28, and engages with the fourth engagement portion 28.

In this process, the elevator shaft 82 provided on the elevator 80 hits the elevator pivot portion 764 provided on the edge of the elevator mounting groove 761 inside the endoscope cap 50. When the user further pushes the endoscope cap 50, the elevator pivot portion 764 rides on the elevator shaft 82. Due to the elastic deformation, the space between the elevator mounting grooves 761 is increased.

The elevator shaft 82 enters the inside of the elevator pivot portion 764. Thereafter, the position of the elevator pivot portion 764 returns to the original position due to the elastic return. As described above, the endoscope cap 50 is mounted to the distal tip of the insertion portion 30.

As illustrated in FIG. 19, the tube-shaped channel 34 is connected to the channel outlet 35 provided at the distal tip 31. The channel outlet 35 spreads in a trumpet shape toward the window portion 53. The curved portion 27 that gently protrudes toward the distal tip side is provided in the vicinity of the third engagement portion 29 of the channel outlet 35, that is, on a peripheral edge portion on a side where the elevator 80 rises as viewed from the channel outlet 35.

Figure 23:
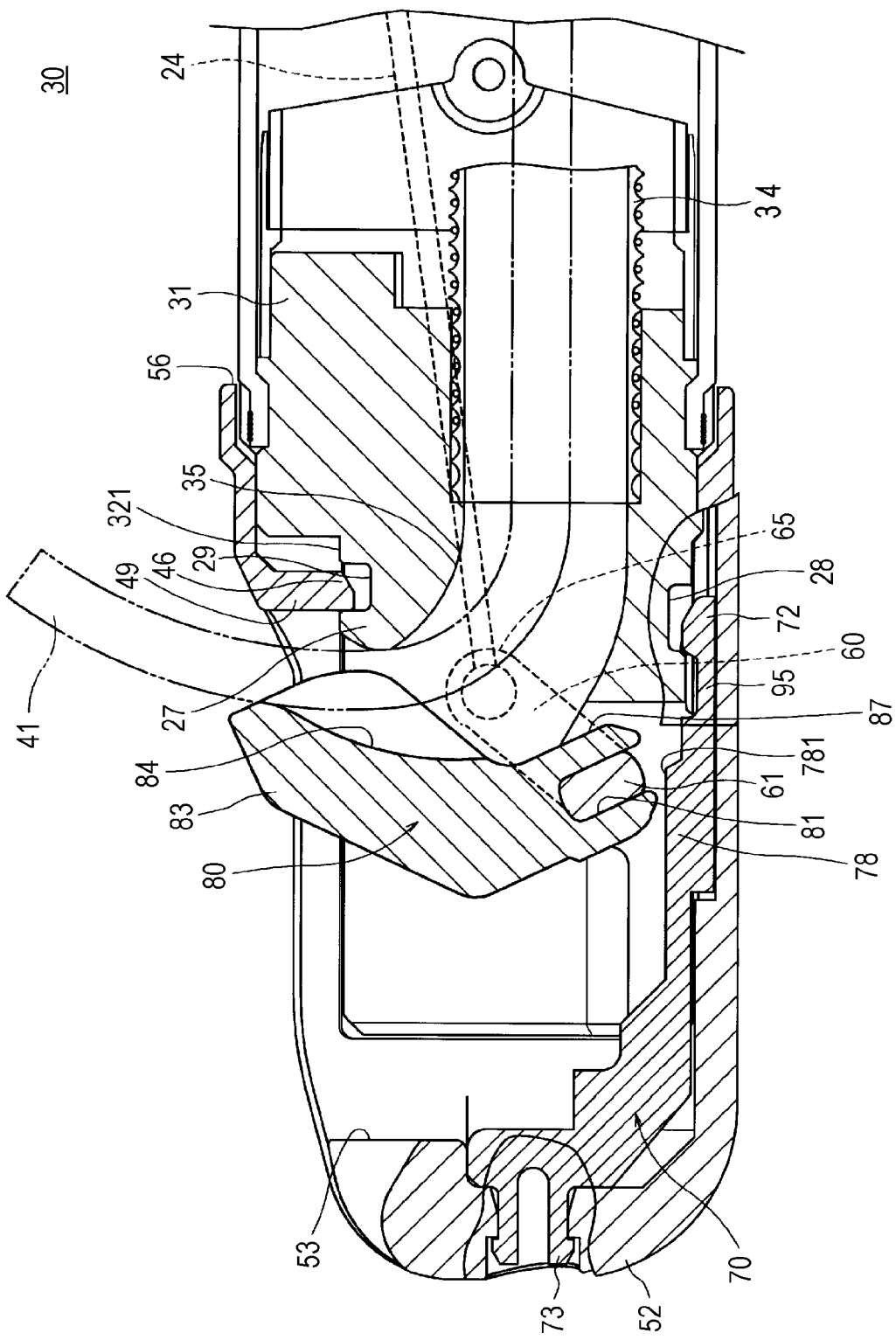
FIG. 23 is a cross-sectional view of the insertion portion with the elevator raised.

FIG. 23 is a cross-sectional view of the insertion portion 30 with the elevator 80 raised. FIG. 23 illustrates the same cross section as FIG. 20. A configuration for raising the elevator 80 will be described with reference to FIGS. 7, 8, 17, 19, 21, and 23.

The lever shaft 63 is inserted through a through-hole provided in the support wall 68 from the lever chamber 69 side, and the elevator base connection portion 61 protrudes to the opposite side of the support wall 68 as illustrated in FIG. 7. As described above, the lever chamber 69 is water-tightly sealed by the O-ring 62 and the lever chamber lid 67. Therefore, body fluid or the like does not adhere to the inside of the lever chamber 69 and a path of the elevation wire 24 during the use of the endoscope 10.

The elevator 80 is housed inside the cover 52 in the state illustrated in FIG. 19. The recessed portion 84 is arranged at a position where the treatment tool distal tip 41 protruding from the channel outlet 35 can be gently curved upward in FIG. 19.

As described above, the lever 60 rotates about the lever shaft 63 as the axis as the user operates the elevation operation lever 21. The elevator base connection portion 61 rotates integrally with the lever shaft 63. As described with reference to FIG. 21, the lever shaft 63 and the elevator shaft 82 are coaxial. Since the elevator base connection portion 61 is connected to the lever connection portion 81, the elevator 80 also rotates integrally with the lever 60. As a result, a distance between the elevator 80 and the window portion 53 changes.

FIG. 23 illustrates a state where the elevator 80 is rotated. The treatment tool distal tip 41 protruding from the channel outlet 35 is raised as being pushed by the elevator 80. The treatment tool distal tip 41 is pushed further into the operation unit side by the edge on the distal tip side of the recessed portion 84 from the state of being pushed against the distal tip of the curved portion 27.

An overview of a method for using the endoscope 10 of this embodiment will be described. The endoscope 10 is stored in a state where the elevator 80 and the endoscope cap 50 have been removed, and cleaning or the like has been performed. The elevator 80 and the endoscope cap 50 are provided in a state of being sealed in a sterilization pack individually or for each set, and then placed in a paper box in units of 10 or 10 sets, for example, and then subjected to electron beam sterilization. The number of the elevators 80 and the endoscope caps 50 to be placed in the paper box is desirably a minimum sales unit, that is, a minimum unit to be sold to the user at one time.

Incidentally, the materials of the cover 52 which is a component of the endoscope cap 50 and the pedestal 70, and the material of the elevator 80 are desirably materials which are highly durable for electron beam sterilization such as polypropylene and polycarbonate of a radiation resistance grade.

The user takes out the elevator 80 from the sterilization pack. The user mounts the elevator 80 to the endoscope 10 according to the above-described procedure. Then, the user takes out the endoscope cap 50 from the sterilization pack. The user mounts the endoscope cap 50 to the insertion portion 30 according to the procedure described above. The user confirms that the endoscope cap 50 is firmly fixed to the distal tip of the insertion portion 30 by lightly pulling the endoscope cap 50 or the like.

The user inserts the insertion portion 30 from a mouth of a person to be examined. The user guides the distal tip of the insertion portion 30 to a target site while observing a captured image through the observation window 36. The user inserts the treatment tool 40 or the like from the channel inlet 22 in accordance with a purpose. After confirming that the treatment tool distal tip 41 protrudes from the distal tip of the insertion portion 30 and is positioned in the vicinity of the target site, the user operates the elevation operation lever 21 to guide the treatment tool distal tip 41 to the target site. After performing a necessary measure and the like, the user removes the treatment tool 40 from the channel 34. The user removes the endoscope 10 from the subject to be examined and ends the examination or treatment.

After the end of the examination or the procedure, the user dismounts the endoscope cap 50 from the endoscope 10 by pushing the cover 52 with two fingers and pulling it toward the distal tip side as described above. As described above, the elevator 80 and the endoscope cap 50 are removed together from the endoscope 10.

Incidentally, it is difficult to consider a case where an external force enough to deform the cover 52 is applied simultaneously at two portions of the cover 52 when observation and treatment are performed using the endoscope 10 by a general method. Since the flange 85 covers one surface of the lever connection portion 81, the rigidity of the lever connection portion 81 is increased. Therefore, when performing observation and treatment using the endoscope 10 in a normal manner, it is unlikely that the lever connection portion 81 is deformed and an external force is applied to the extent that the lever connection portion 81 is disengaged from the elevator base connection portion 61.

The user performs processing such as cleaning on the endoscope 10 after removing the endoscope cap 50 and the elevator 80 in preparation for the next use. The elevator base connection portion 61 used for fixing the elevator 80 is exposed at the distal tip 31 as illustrated in FIG. 7.

As described above, the endoscope 10 of this embodiment does not need any special cleaning work or the like to clean the complicated structure in the vicinity of the elevator 80. As described above, since the body fluid or the like does not adhere to the inside of the lever chamber 69 and the path of the elevation wire 24 during the use of the endoscope 10, cleaning of these portions is not required.

Therefore, it is possible to provide the endoscope 10 with the elevator which can be operated efficiently with a short processing time between cases. According to this embodiment, operability at the time of ending an endoscopic examination procedure can be improved, that is, the operation of dismounting the endoscope cap 50 and the elevator 80 from the endoscope 10 at the same time, and easy cleaning of the endoscope 10 both can be made compatible.

The endoscope 10 of this embodiment is provided with the elevator 80 and is the side-view type, and thus, is suitable for diagnosis and treatment of duodenum and a pancreaticobiliary region. In particular, the endoscope 10 of this embodiment is suitable when performing procedures such as endoscopic retrograde cholangio pancreatography (ERCP), endoscopic sphincterotomy (EST), and endoscopic biliary drainage (EBD). This is because the treatment tool 40 is guided inside duodenal papilla on a duodenal wall and a pancreatic duct and a common bile duct which are open to the duodenal papilla to perform treatment and the like in these procedures.

Incidentally, the side-view type endoscope 10 is sometimes referred to as a side-view endoscope. Similarly, the endoscope 10 suitable for diagnosis of the duodenum and pancreaticobiliary region is sometimes referred to as a duodenoscope.

According to this embodiment, the pedestal 70 and the cover 52 are separate bodies, and thus, have simple shapes. Thus, it possible to produce the pedestal 70 and the cover 52 at low cost by, for example, injection-molding or the like.

The user may select and use the endoscope cap 50 having a specification corresponding to a procedure from a plurality of types of the endoscope caps 50 having different specifications. For example, when using expensive and precise equipment such as an ultrasonic probe or an ultra-fine endoscope in combination, an endoscope cap 50 having a function of limiting the rotation range of the elevator 80 narrow to prevent damage to the equipment due to excessive bending may be provided.

The recessed portion 84 provided in the elevator 80 has a function of holding the treatment tool distal tip 41 and making it hard to shake right and left. The user may select and use the elevator 80 having specifications according to the procedure from a plurality of types of elevators 80 having different shapes of the recessed portions 84. For example, in a procedure that requires precise manipulation of a thin treatment tool 40 such as a guide wire, an elevator 80 having a recessed portion 84 suitable for the thin treatment tool 40 is used.

In this manner, it is possible to provide the endoscope 10 which enables the user to select and use the elevator 80 and the endoscope cap 50 suitable for an application. Further, the elevator 80 and the endoscope cap 50 of the combination recommended for each application may be provided as a set.

The endoscope 10 may be a so-called endoscopic ultrasonography including an ultrasonic transducer at a distal tip thereof. In this case, the endoscope cap 50 desirably has a hole through which the ultrasonic transducer is inserted, at a bottom thereof. The endoscope 10 may be an endoscope for a lower gastrointestinal tract. The endoscope 10 may be a so-called rigid scope provided with the rigid insertion portion 30. The endoscope 10 may be a so-called industrial endoscope used for an examination of an engine, piping, and the like.

The endoscope cap 50 and the elevator 80 of this embodiment are each a so-called single use, and are discarded after being used once.

The endoscope cap 50 may be reusable. In this case, the user dismounts the elevator 80 from the endoscope cap 50 dismounted from the insertion portion 30. The endoscope cap 50 is visually inspected by the user, and if it is not damaged, the endoscope cap 50 is subjected to processing such as cleaning and reused. Since the opening end portion 56 of the endoscope cap 50 is widely open, the processing such as cleaning can be easily performed as compared with the state of being mounted to the insertion portion 30. Since the endoscope cap 50 is small, it is also easy to place the endoscope cap 50 in the sterilization pack, for example, and perform autoclave sterilization or the like.

After disassembling the endoscope cap 50 into the cover 52 and the pedestal 70, a process such as cleaning may be performed, and the endoscope cap 50 may be reused after being reassembled. By disassembling, cleaning and the like can be performed more reliably.

The elevator 80 may be reusable. In this case, the user visually inspects the elevator 80 dismounted from the endoscope cap 50, and performs processing such as cleaning for the reuse when there is no damage. Since the elevator 80 is small, it is also easy to place the elevator in the sterilization pack, for example, and perform autoclave sterilization or the like. If reusable, the elevator 80 may be made of a highly durable material such as metal or ceramics.

The lever connection portion 81 may have the same retainer at the end of the opening as the elevator pivot portion 764. After the elevator base connection portion 61 and the lever connection portion 81 are engaged, the endoscope cap 50 can be easily mounted before the endoscope cap 50 is attached without worrying about that the elevator 80 comes off. In this case, the retainer on the lever connection portion 81 side is detached with a weaker force than the retainer on the elevator mounting groove 761 side.

Second Embodiment

This embodiment relates to the endoscope 10 having the endoscope cap 50 that can be easily mounted. Descriptions regarding common parts with the first embodiment will be omitted.

Figure 24:
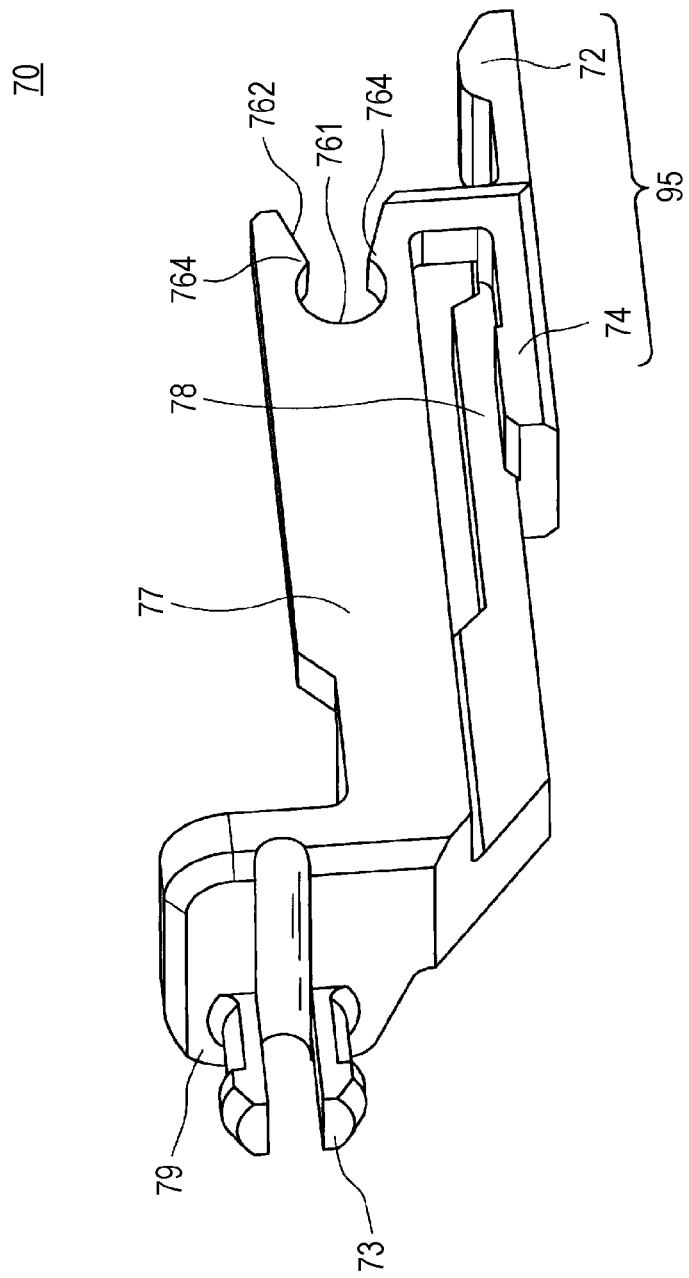
FIG. 24 is a perspective view of the pedestal according to a second embodiment.

FIG. 24 is a perspective view of the pedestal 70 according to the second embodiment. On the side surface of the elevator mounting groove 761, an elevator pivot portion 764 protruding oppositely is provided. A tapered portion 762 is provided outside the elevator pivot portion 764 of the elevator mounting groove 761. The tapered portion 762 has a shape that expands away from the elevator pivot portion 764.

Figure 25:
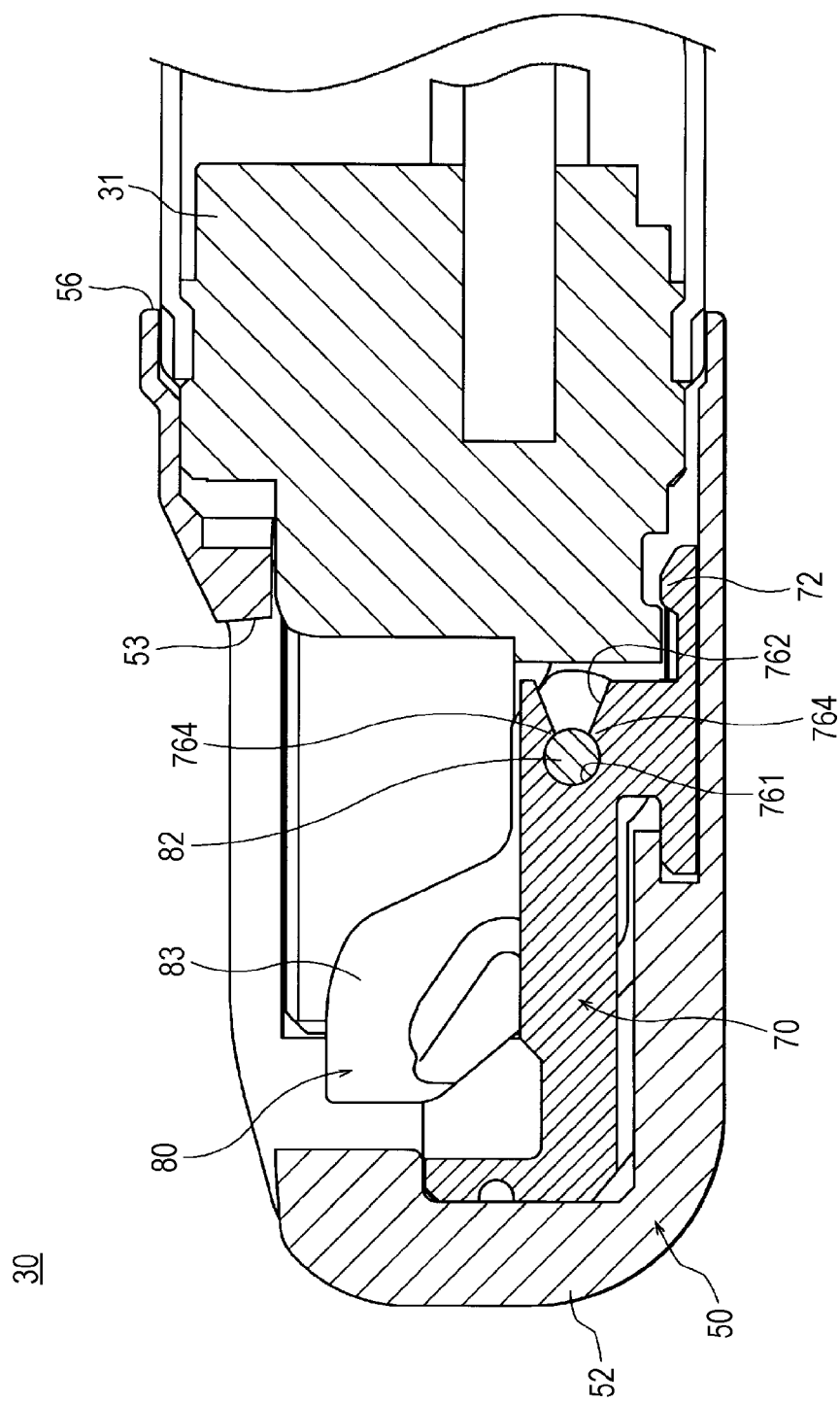
FIG. 25 is a cross-sectional view of the insertion portion of the second embodiment.

FIG. 25 is a cross-sectional view of the insertion portion 30 of the second embodiment. The elevator shaft 82 is rotatably held between the bottom of the elevator mounting groove 761 and the elevator pivot portion 764.

When the user mounts the endoscope cap 50 to the distal tip of the endoscope 10, the tapered portion 762 guides the elevator shaft 82. When the user pushes the endoscope cap 50, the pedestal 70 is elastically deformed, and the space between the elevator pivot portions 764 is increased. The elevator shaft 82 passes through the space between the elevator pivot portions 764, and enters the inside of the elevator pivot portions 764. Thereafter, the elevator pivot portion 764 returns to the original state due to the elastic return.

According to this embodiment, it is possible to provide the endoscope 10 having the endoscope cap 50 that can be easily mounted. Further, similarly to the first embodiment, it is possible to provide the endoscope 10 having the endoscope cap 50 and the elevator 80 that can be easily dismounted.

Technical features (constitutional requirements) described in the respective embodiments can be combined with each other, and new technical features can be formed with the combination.

The embodiments disclosed herein are exemplary in all respects, and it should be considered that the embodiments are not restrictive. The scope of the invention is defined not by the above-described meaning but by claims, and intends to include all modifications within meaning and a scope equal to claims.

REFERENCE SIGNS LIST

10 endoscope
12 soft portion
13 bending section
20 operation unit
21 elevation operation lever
22 channel inlet
23 bending knob
24 elevation wire (rotating portion)
27 curved portion
28 fourth engagement portion
29 third engagement portion
30 insertion portion
31 distal tip portion
321 first flat surface portion
322 second flat surface portion
323 third flat surface portion
33 optical housing portion
34 channel
35 channel outlet
36 observation window
37 illumination window
38 nozzle
40 treatment tool
41 treatment tool distal tip
45 pedestal groove
46 first engagement portion
461 first wedge surface
462 second wedge surface
48 recess
49 protruding portion
50 endoscope cap
52 cover
53 window portion
56 opening end portion
57 pedestal fixing hole
58 second fixing protrusion
60 lever
61 elevator base connection portion
62 O-ring
63 lever shaft
64 rotating connection portion
65 wire fixing portion
66 cap screw
67 lever chamber lid
68 support wall 69 lever chamber
70 pedestal
72 second engagement portion
73 first fixing protrusion
741 thick plate
761 elevator mounting groove (elevator support portion)
762 tapered portion
764 elevator pivot portion
77 first wall
78 second wall
79 third wall
80 elevator
81 lever connection portion
82 elevator shaft
83 elevation portion
831 first elevation portion
832 second elevation portion
84 recessed portion
85 flange
93 first cavity portion
94 second cavity portion
95 base portion

The invention claimed is:

1. An endoscope, comprising:
a lever that is rotatably provided at a distal tip of an insertion portion;
an elevator that can be attached to and detached from the distal tip of the insertion portion, and includes a lever connection portion connected to the lever, and an elevator shaft arranged to rotate coaxially with the lever when the lever connection portion and the lever are connected; and
an endoscope cap that can be attached to and detached from the distal tip of the insertion portion, and includes a bottomed cylindrical cover, an elevator support portion that is provided inside the cover and has an inlet through which the elevator shaft enters when mounted to the distal tip of the insertion portion, and an elevator pivot portion provided at the inlet, wherein the bottomed cylindrical cover has an opening end portion and can attach and detach the opening end portion with respect to the distal tip of the insertion portion,
wherein the elevator support portion is a U-shaped groove that has an opening toward the opening end portion.

2. The endoscope according to claim 1,
wherein the lever connection portion is a groove that engages with the lever.

3. The endoscope according to claim 2,
wherein the lever connection portion has one end surface of the groove closed.

4. An endoscope cap capable of being attached to and detached from an endoscope that includes a lever provided rotatably at a distal tip of an insertion portion of the endoscope, and a rotating portion for rotating the lever, and mounted in an elevator that includes an elevation portion having a recessed portion on one surface, a lever connection portion provided at an end portion of the elevation portion and connected to the lever, and an elevator shaft arranged to rotate coaxially with the lever when the lever connection portion and the lever are connected to each other, the endoscope cap comprising:
a bottomed cylindrical cover that has an opening end portion, and can attach and detach the opening end portion with respect to the distal tip of the insertion portion of the endoscope;
an elevator support portion that has an inlet through which the elevator shaft enters when fixed to an inside of the cover and mounted to the distal tip of the insertion portion; and
an elevator pivot portion that is provided at the inlet,
wherein the elevator support portion is a U-shaped groove that has an opening toward the opening end portion.

5. A mounting method of an endoscope cap, comprising:
holding an insertion portion of an endoscope having a lever rotatably provided at a distal tip of the insertion portion;
connecting a lever connection portion of an elevator to the lever, the elevator including an elevation portion having a recessed portion on one surface, the lever connection portion provided at an end portion of the elevation portion and connected to the lever, and an elevator shaft arranged to rotate coaxially with the lever when the lever connection portion and the lever are connected; and
mounting the endoscope cap to the distal tip of the insertion portion, the endoscope cap including a bottomed cylindrical cover having an opening end portion and capable of attaching and detaching the opening end portion with respect to the distal tip of the insertion portion of the endoscope, an elevator support portion having an inlet through which the elevator shaft enters when fixed inside the cover and mounted to the distal tip of the insertion portion, and an elevator pivot portion provided in the inlet, wherein the elevator support portion is a U-shaped groove that has an opening toward the opening end portion.

6. A dismounting method of an endoscope cap from an endoscope that includes an insertion portion rotatably provided at a distal tip, an elevator that can be attached to and detached from a distal tip of the insertion portion, and includes a lever connection portion connected to the lever, and an elevator shaft arranged to rotate coaxially with the lever when the lever connection portion and the lever are connected, and the endoscope cap that can be attached to and detached from the distal tip of the insertion portion, and includes a bottomed cylindrical cover, an elevator support portion that is provided inside the cover and has an inlet through which the elevator shaft enters when mounted to the distal tip of the insertion portion, and an elevator pivot portion provided at the inlet, wherein the bottomed cylindrical cover has an opening end portion and can attach and detach the opening end portion with respect to the distal tip of the insertion portion of the endoscope, and the elevator support portion is a U-shaped groove that has an opening toward the opening end portion, the method comprising:
holding the insertion portion; and
pulling the cover toward a distal tip side of the insertion portion to dismount the endoscope cap and the elevator integrally from the insertion portion.

* * * * *